(12) United States Patent
Bata et al.

(10) Patent No.: US 10,022,350 B2
(45) Date of Patent: Jul. 17, 2018

(54) ANTIBACTERIAL MICROELEMENT CHELATES AND THE USE THEREOF IN ANIMAL FEEDS

(71) Applicant: Dr. Bata Zrt., Kecskemét (HU)

(72) Inventors: Árpád Bata, Ócsa (HU); József Kutasi, Göd (HU)

(73) Assignee: Dr. Bata Zrt., Keeskemét (HU)

( * ) Notice: Subject to any disclaimer, the term of this patent is extended or adjusted under 35 U.S.C. 154(b) by 0 days.

(21) Appl. No.: 14/411,630

(22) PCT Filed: May 28, 2013

(86) PCT No.: PCT/IB2013/054391
§ 371 (c)(1),
(2) Date: Dec. 29, 2014

(87) PCT Pub. No.: WO2014/001924
PCT Pub. Date: Jan. 3, 2014

(65) Prior Publication Data
US 2015/0157594 A1 Jun. 11, 2015

(30) Foreign Application Priority Data

Jun. 29, 2012 (HU) .................................... 1200394

(51) Int. Cl.
| | | |
|---|---|---|
| A61K 31/315 | (2006.01) | |
| A61K 31/19 | (2006.01) | |
| A61K 31/194 | (2006.01) | |
| A61K 31/198 | (2006.01) | |
| A61K 31/28 | (2006.01) | |
| A61K 31/295 | (2006.01) | |
| A61K 31/30 | (2006.01) | |
| A61K 33/02 | (2006.01) | |
| C07F 1/08 | (2006.01) | |
| C07F 3/06 | (2006.01) | |
| C07F 13/00 | (2006.01) | |
| C07F 15/02 | (2006.01) | |
| A23K 20/105 | (2016.01) | |
| A23K 20/142 | (2016.01) | |
| A23K 20/158 | (2016.01) | |
| A23K 20/10 | (2016.01) | |
| A23K 20/195 | (2016.01) | |
| A23K 20/20 | (2016.01) | |
| A23K 50/10 | (2016.01) | |
| A23K 50/75 | (2016.01) | |
| A23K 50/30 | (2016.01) | |
| A23K 50/60 | (2016.01) | |
| A23L 33/165 | (2016.01) | |

(52) U.S. Cl.
CPC ............ *A61K 31/315* (2013.01); *A23K 20/10* (2016.05); *A23K 20/105* (2016.05); *A23K 20/142* (2016.05); *A23K 20/158* (2016.05); *A23K 20/195* (2016.05); *A23K 20/20* (2016.05); *A23K 20/30* (2016.05); *A23K 50/10* (2016.05); *A23K 50/30* (2016.05); *A23K 50/60* (2016.05); *A23K 50/75* (2016.05); *A23L 33/165* (2016.08); *A61K 31/19* (2013.01); *A61K 31/194* (2013.01); *A61K 31/198* (2013.01); *A61K 31/28* (2013.01); *A61K 31/295* (2013.01); *A61K 31/30* (2013.01); *A61K 33/02* (2013.01); *C07F 1/08* (2013.01); *C07F 3/06* (2013.01); *C07F 13/005* (2013.01); *C07F 15/02* (2013.01)

(58) Field of Classification Search
CPC .... A61K 31/315; A61K 31/194; A61K 31/28; A61K 31/295; A61K 31/30; A61K 31/19; A61K 31/198
See application file for complete search history.

(56) References Cited

U.S. PATENT DOCUMENTS

| | | |
|---|---|---|
| 6,323,354 B1 | 11/2001 | Moore |
| 2003/0152508 A1 | 8/2003 | Nip |
| 2005/0283013 A1 | 12/2005 | Lee et al. |
| 2007/0269495 A1 | 11/2007 | Ashmead |
| 2007/0293466 A1 | 12/2007 | Thompson |
| 2008/0057136 A1 | 3/2008 | Polyakov et al. |

FOREIGN PATENT DOCUMENTS

| | | |
|---|---|---|
| CN | 1484971 A | 3/2004 |
| CN | 101744120 A | 6/2010 |
| CN | 101838214 A | 9/2010 |
| CN | 101941931 A | 1/2011 |
| CN | 102150751 A | 8/2011 |
| CN | 102318764 A | 1/2012 |
| EP | 2 668 849 A1 | 4/2013 |
| RU | 2 229 897 C2 | 6/2004 |
| WO | 2004/080210 A1 | 9/2004 |

OTHER PUBLICATIONS

Kim et al.: "Effect of supplemental copper-methionine chelate and copper-soy proteinate on the performance, blood parameters, liver mineral content, and intestinal microflora of broiler chickens", J. Appl. Poult. Res., 2011, vol. 20, pp. 21-32.

(Continued)

*Primary Examiner* — Sudhakar Katakam
(74) *Attorney, Agent, or Firm* — Jason D. Voight

(57) ABSTRACT

The present invention relates to a microelement organic O-chelate or N-chelate complex compound, for the inhibition of facultative pathogenic bacteria. The present invention further relates to a composition, feed additive or feed comprising the compounds, as well as methods for the preparation thereof, and for the use thereof in animal stock farming.

12 Claims, 2 Drawing Sheets

(56) References Cited

OTHER PUBLICATIONS

Stánilá et al.: "Antibacterial activity of copper and cobalt amino acids complexes", Not. Bot. Horti Agrobo., 2011, vol. 39(2), pp. 124-129.
Hutjens: "Importance of trace minerals in dairy heifer, dry cow, and lactating cow rations", Illini Dairy Net Papers, 1999.
Feng et al.: "A mechanistic study of the antibacterial effect of silver ions on *Escherichia coli* and Staphylococcus aureus", J. Biomed. Mater. Res., 2000, vol. 52(4), pp. 662-668.
Sun et. al:"The exploration of the antibacterial mechanism of $Fe^{3+}$ against bacteria" Brazilian Journal of Microbiology, 2011, vol. 42, pp. 410-414.
Ashmead et. al.: "Increasing Protein/Energy Digestion by Feeding Metal Amino Acid Chelates", Intern. J. Appl. Res-Vet. Med., 2008, vol. 6, No. 1., pp. 38-45.
Wang et al.: "Dietary zinc glycine chelate on growth performance, tissue mineral concentrations, and serum enzyme activity in weanling piglets", Biol. Trace. Elem. Res., 2010, vol. 133, pp. 325-334.
Yu et al.: "Effects of zinc source and phytate on zinc, absorption by in situ ligated intestinal loops of broilers", Poultry Science, 2010, vol. 89, pp. 2157-2165.
Kinal et al.: "The influence of administration of biotin and zinc chelate (Zn-methionine) to cows in the first and second trimester of lactation on their health and productivity", Polish Journal of Veterinary Sciences, 2011, vol. 14, No. 1, pp. 103-110.
Chu et al.: "Siderophore uptake in bacteria and the battle for iron with the host; a bird's eye view", Biometals, 2010, vol. 23(4), pp. 601-611.
Miethke et al.: "Siderophore-Based Iron Acquisition and Pathogen Control", Microbiol. Mol. Biol. Rev., 2007, vol. 71(3), pp. 413-451.
Weger et al.: "Siderophores and outer membrane proteins of antagonistic, plant-growth-stimulating, root-colonizing *Pseudomonas* spp.", J. Bacteriol., 1986, vol. 165(2), pp. 585-594.
Whittaker et al.: "Toxicological Profile, Current Use, and Regulatory Issues on EDTA Compounds for Assessing Use of Sodium Iron EDTA for Food Fortification", Regul. Toxicol. Pharmacol., 1993, vol. 18(3), pp. 419-427.
Zhang et al.: "Syntheses, spectroscopies and structures of zinc complexes with malate", Inorganica Chimica Acta, 2009, vol. 362, pp. 2643-2649.
Sadikov et al.: "Crystal Structure of Zinc(II) Hydrated Trinuclear Complex with Monoprotonated Ethylenediaminetetraacetate Anion(3−), [ZN3(HEdta)2(H2O)6]", Crystallography Reports, 2004, vol. 49, pp. 990-997.
Gelabert et al.: "Hydrothermal synthesis and extended structure of poly[aqua(mu5-ethylene-diaminetetraacetato) dizinc(II)]", Acta Crystallographica, 2010, pp. m327-m329.

ANTIBACTERIAL MICROELEMENT CHELATES AND THE USE THEREOF IN ANIMAL FEEDS

This is the national stage of International Application PCT/IB2013/054391, filed May 28, 2013.

The present invention relates to microelement organic chelate complex compound, for the inhibition of facultative pathogenic bacteria. The present invention further relates to a composition, feed additive or feed comprising the compounds, as well as methods for the preparation thereof, and for the use thereof in animal stock farming.

Minerals play a diverse and essential role in the physiological and biochemical operations of living organisms. They are components of enzymes (Zn, Cu, Mn, Mg, Fe) and vitamins (Co), among others. They have definitive a role in different protective mechanisms (Cu, Zn, Fe, Se). They play a role in hematopoiesis (Cu, Fe), reproduction (P, Cu, K, Mn, Zn, Mg). They facilitate the synthesis of nucleic acids and proteins. The mineral content of fodder crops depends on several factors, such as the taxonomical place of the plant, the composition and pH of the soil, the yearly distribution of precipitation, agronomical technology, and shows very high variability. In the dry periods, the mineral content of fodder crops decreases. It increases at the beginning of the phenologic phase of the plants, then after reaching a maximum, starts to decrease. The leaching away occurring at harvest or in the case of vexillar plants' leaf loss also accompanied by significant mineral content loss. During replenishment of the soil, abandoning the use of livestock manure disrupted the recirculation equilibrium of the soil, the soils continue to be acidified, and weakened.

Amongst the livestock animals, for the determination of mineral demands of fodder eating animals (swine, poultry), we can now lean better on the mineral content of the fodder crops, as provided in feeding tables, than in the case of roughage eating ones. In the germinal parts of the plants, such as seeds, the mineral content fluctuation is less profound than in the vegetative parts, such as stems, leafs. But even with this, the variation may be 2-3-fold in the case of seeds. However, livestock bred to high yield require an increased and equilibrated mineral (including microelement) supplementation. At present, this requirement is solely satisfied through the feed by admixing trace elements into the feed provided, mainly using different mineral salts.

The level of the required supplementation cannot be planned without knowing the composition of the basic feed and the amount of additional fodder. The requirements are different depending on the species, age group, utilization types. The lack of mineral supply in the feed can be determined in two ways. Primary deficiency is when the given element is scarce in the feed. Secondary deficiency occurs when the body cannot utilize the element added to the feed, for example a factor necessary to absorb it is missing, or the dominance of antagonistic elements inhibits the absorption of the given elements. (Kakukk-Schmidt, 1988).

The trace elements belong to the group mineral compounds, metallic or non metallic elements occurring in the very minute amounts in the plant or animal body. Based on their function, they may function as static, homeostatic, or enzymatic (Fe, Zn, Cu, Mn, Mo, I, Ni, Se, Cr) elements. In the case of their deficiency, they may be categorized as essential elements, however, in high concentration they may be toxic. Therefore certain trace element may be essential or toxic, depending on the concentration of which it is present in the organism (Kakukk-Schmidt, 1988). The minerals may be absorbed in ionized form, as cations or anions, or coupled to a carrier protein, or by active transport within the organism (except for the potassium). The ions of metals can form reversibly bound metallic complexes with electron donor ligands, these are the so called chelates. This process consumes significant amount of ATP (Kakukk-Schmidt, 1988). The positively charged metal ion acts as a Lewis acid in aqueous environment, and this way capable to react with an electron donor (Lewis base) while a complex, coordinated compound or coordinated ion is formed. The electrostatic effect of the chelates can only by observed in aqueous phase (aquachelates). Thus otherwise insoluble compounds become absorbable after solubilized in the form of metallic complexes. Earlier studies, with humic acid, and humochelates produced with alga hydrolizates, or alginates, proved that the metallic chelates are utilized better than the metal salts. They did not spread widely because although less is required, the cost of production was very high (Kakukk-Schmidt, 1988).

The biological effect of the elements is largely influenced by the chemical form thereof. Metal salts, such as chlorides, sulfates are utilized better than the oxides or carbonates (Kakukk-Schmidt, 1988). The factories producing premixes use the inorganic forms of microelements, despite the fact that these elements are present in the plants mainly in organic compounds. The scientific research of the past 10-15 years made it clear that using microelements in organic bounds is advantageous compared to the inorganic forms. The metal-containing organic complex is one of the main compound form in biological systems. The metal ion occupies the central position in the complexes, ions, molecules, natural organic compounds (amino acids, peptides, proteins, carbohydrates, etc.), i.e. ligands attach thereto. The chemical reaction between certain ions and organic compounds produces chelates, when the metal ion is attached to two or more atoms of a ligand. Chelate compounds with metal—ligand interactions are the most valuable to the organism, because the activity of the metals in these complexes $10^5$-$10^7$-fold higher than in ionized form.

The chelates may be transfer, storage and metabolic chelates based on their functions. The metabolic chelates are compounds with porphyrin scaffold (such as hemoglobin, chlorophyll), with $Fe^{2+}$, $Cu^{2+}$ ions within their cores, among others. The transfer chelates are usually amino acids (gyicine, cystine, histidine), and rarely may also be peptides (Kakukk-Schmidt, 1988). In the case of most microelements the following chelate complexes are formed: complexes formed with amino acids, proteins, organic acids, etc. out of which the protein (amino acid) microelement complexes are elementary. In order to decrease the sufficient $Fe^{2+}$, $Mn^{2+}$, $Cu^{2+}$, $Zn^{2+}$ and $Cr^{3+}$ ion requirement for the animals, better utilized feed additives are necessary than the currently available one on the stock raising field. It is known from the literature that the trace element provided in organic form is utilized better, but the level of utilization depends on the chemical structure of the compound used. Besides the better microelement utilization, in the case of a trace element admixed to the feed, the interaction of the elements may be decreased significantly (Du, 1994, Shi et al., 1995, Mahan, 1997).

According to the results of studies and practical experiences, the absorption and biological effect of trace elements in organic bounds is more advantageous, however the amounts suitable to satisfy the requirements must be determined for each trace elements and animal species. This is even more important because the maximum level of the trace element administrable within the feed, quite rightly so, is continuously decreasing due to the rigorous food safety and environmental regulations. The decrease means in some cases that the trace element need of the animal can only be satisfied with superior or better absorbed trace element supply.

At the same time, several inorganic compounds has an antibacterial effect (such as copper sulfate, zinc oxide). In our own experience, we found with metal containing products (Se—yeast products) that metal complexes in organic bound has also had antibacterial properties. However, this effect is not practically useful, because the level of trace element used is toxic for the animals. A similar effect of $CuSO_4$ and ZnSO4 is also used during industrial fermentation, where the toxic trace element concentration is more permissive. Whittaker and coworkers (1993) found in their experiments that metal compounds containing metal salts in chelate bounds are useful for example against *Helicobacter pylori*. Similar findings are reported in U.S. Pat. No. 6,429, 225. It should be noted that the *Helicobacter pylori* is a peculiar pathogen for several reasons, for example that it is present within the highly acidic environment of the stomach. Accordingly, no definitive conclusion may be drawn from the anti-*Helicobacter pylori* properties of prior art chelates on whether and how the bacteria in general present in the intestinal flora would react to the organic metal chelate compounds, and what types of these should be tried, if at all.

Several patent applications disclose the use of metal chelate complexes in stock farming.

Patent application No. CN1484971A (SHUIAZHUANG CITY KEXING ANIMA; 2004 Apr. 31) discloses an animal feed containing amino acid metal chelate complexes. The chelate complex comprises iron, copper, manganese and zinc amino acid chelate, among others.

Patent application No. CN101941931A (HUBEI SHENZHOU CHEMICAL CO LTD.; 2011 Jan. 12) discloses a method for the preparation of methionine metal chelates. Methionine and a soluble metal salt (e.g. copper sulfate, copper chloride, zinc sulfate, zinc chloride, chromium trichloride, iron sulfate, iron chloride) is mixed together in the presence of alcohol, and the mixture is kept at 40-150° C. for 1-8 hours, then it is filtered and dried. The methionine metal chelate is used in animal feed.

Patent application No. CN101838214A (INST. OF SUBTROPICAL AGRICULTURE CHINESE ACADEMY OF SCIENCES; 2010 Sep. 22) discloses a method for the preparation of DL-threonine copper chelate. The DL-threonine copper chelate is prepared form glycine copper chelate and acetaldehyde. The DL-threonine copper chelate is also used in animal feed.

Patent application No. CN101744120A (UNIV. HEBEI AGRICULTURE; 2010 Jun. 23) discloses a trace element feed prepared for sucking piglets. The feed comprises iron bis-glycinate chelate, zinc glycinate, copper glycine, magnesium sulfate, potassium iodide and yeast.

Patent application No. CN102150751A (TANGSHAN NORMAL UNIVERSITY; 2011 Aug. 17) discloses a premix useful in feeds for furred animals. The premix comprises, among others, iron, zinc, manganese, copper, selenium amino acid chelates, and is preferably used during the pregnancy and nursing period of furred animals.

The object of the above documents is the preparation of metal compounds with better absorption properties.

WO 2009/066117 discloses the use of EDTA or salts thereof for the treatment of swine dysentery caused by *Brachyspira hyodysenteriaea*.

WO2004/080210 discloses zinc and copper metal salts and simple complexes of inorganic acids and organic acids, as well as antimicrobial properties thereof, by making them non-absorbent within the first segments of the digestive tract with a micro-encapsulation process.

Our new finding in the mechanism of action of organic chelates is that certain complex compounds—by themselves or in combination—are capable to inhibit the proliferation of pathogenic bacteria within the intestinal tract, therefore allowing for the predominince of useful members of the normal intestinal flora (*Lactobacillus, Lactococcus, Bifidobacterium*). The prior art did not suggest an antibacterial effect for the amino acid trace element chelate complexes.

Accordingly, the present invention relates to a microelement organic chelate complex, for the inhibition of pathogenic bacteria, having the general formula

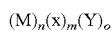

wherein M is Zn, Cu, Fe, Mn, Ag;
X is $NH_4$, $H_2O$;
Y is amino acid, fatty acid, hydroxy acid and/or polyamino carboxylic acid;
n is 0-6;
in is 1-6;
o is 1-8.

WO 2009/066117 discloses the use of EDTA or salts thereof for the treatment of swine dysentery caused by *Brachyspira hyodysenteriaea*. The efficiency of EDTA or sodium EDTA used therein is inferior to the efficiency of the microelement EDTA water chelate complexes or microelement EDTA ammonium chelate complexes according to the present invention. The chelate complexes formed with the water molecules or ammonium molecules result in such an advantageous chelate structure that acts as siderophore analogs and/or antibiotic binding and/or QS signal molecule binding molecules, and inhibit the pathogenic bacteria at a minimal concentration, about 10-500 mg/kg.

In contrast to WO2004/080210, where the compounds exert their antimicrobial effect by being non-absorbent in the first segment of the digestive tract due to their micro encapsulation, the present invention is based on the finding that if besides the complexes of trace elements we prepare the O- and N-chelates thereof, then the microbiological activity of the special compounds thus formed is much higher than that of the simple complexes of these microelements. According to this novel finding, in addition to the O- and N-chelate complex forming compound, a water molecule or another O-chelate forming, or ammonium or another N-chelate forming molecule should be present in dative bond, depending on the microorganism.

The amino acid used is preferably selected from the group consisting of the 20 naturally occurring amino acids.

The fatty acid used is preferably selected from the group consisting of formic acid, acetic acid, propionic acid and butyric acid.

The hydroxy acid used is preferably malic acid or lactic acid.

The polyamino carboxylic acid is preferably nitrilotriacetic acid or ethylenediamine tetraacetic acid.

In a further embodiment, the present invention relates to a compound, wherein the pathogenic bacterium is selected from the group consisting of: *Salmonella enterica, Salmonella enterica* subp. *Enterica serovar enteritidis, Salmonella typhimurium, Salmonella infantis, Salmonella gallinarium, S. paratyphi, S. abortus-equi, S. java, S. cholerae, S. typhisuis, S. sendai, Escherichia coli, Clostridium perfringens Clostridium barati, Cl. sordellii, Cl. botulinum* A-F, *C. novyy* A, B, C, D, *Cl. septicum, Cl. chuvoei, Cl. hystoliticum, C., sporogenes, Cl. tetani, Brachyspira hyodysenteriaea,*

*Brachyspira pilosicoli, Arcanobacterium piogenes, Staphylococcus aureus, Streptococcus agalactiae, Lawsonia intracellularis.*

In a preferred embodiment the present invention relates to a compound, for the treatment or prevention of a disease selected from the group consisting of: poultry enteric diseases, swine enteric diseases, bovine enteric diseases, as well as superficial treatments, for example ulcerative pododermatitis with necrotic dermatitis of poultry, mastitis of dairy cattle, metritis of dairy cattle, hoof lesions of ungulates, enteric and superficial diseases of other animals.

In a particularly preferred embodiment, the present invention relates to a compound, selected from the group consisting of: zinc tetraamonium bis-glycinate chelate, zinc maleinate chelate, zinc diammonium maleinate chelate, zinc tetraammonium maleinate chelate, zinc diammonium methionate chelate, copper diammonium lysinate chelate, zinc diammonium aminate chelate, preferably zinc monoglycinate chelate, zinc diglycinate chelate, zinc bis-glycinate chelate, copper mono-glycinate chelate, copper di-glycinate chelate, copper bis-glycinate chelate, zinc diammonium bis-maleinate chelate, zinc bis-maleinate chelate, copper bis-maleinate chelate, copper diammonium (maleinate)$_2$ chelate, more preferably zinc mono-glycinate chelate, copper mono-glycinate chelate, zinc diammonium bis-maleinate chelate, copper diammonium (maleinate)$_2$ chelate, zinc diammonium ethylenediamine tetraacetic acid chelate, copper diammonium ethylenediamine tetraacetic acid chelate, most preferably copper diammonium bis-maleinate chelate, zinc diammonium ethylenediamine tetraacetic acid chelate, copper ethylenediamine tetraacetic acid chelate. In the case of the above compounds, the chelate denomination includes, in addition of the salt, the so called O-chelate, for example $H_2O$, or so called N-chelate, for example ammonium.

In a further embodiment, the present invention relates to a compound, for the inhibition of bacteria proliferating and causing diseases in the small intestine part of the digestive tract and/or for the prevention or treatment of diseases caused by said bacteria.

In another aspect, the present invention provides a composition comprising the compound according to the invention, optionally together with standard additives.

In a further preferred embodiment, the present invention provides a composition comprising at least two, synergistically acting compound according to the invention, optionally together with standard additives.

In particularly preferred embodiments, the composition comprises at least three, at least four, at least five, at least six, at least seven, at least eight or more different, synergistically acting compound according to the invention, optionally together with standard additives.

In another aspect, the present invention provides a feed additive, comprising the compound or composition according to the invention.

In a further embodiment, the invention relates to a feed additive, being present on a suitable carrier in a releasable form, preferably a granulate.

In a still further embodiment, the invention relates to a feed, comprising the compound, composition or feed additive according to the invention.

In a further embodiment, the present invention relates to a method for preparing a feed additive, said method comprising admixing the compound or composition according to the invention, and optionally further standard feed additive components.

In a still further embodiment, the present invention relates to a method for preparing a feed, said method comprising mixing the compound, composition or feed additive according to the invention into standard feed.

In another embodiment, the present invention relates to the use of a compound, composition, feed additive or feed according to the invention in stock farming for increasing body-weight gain and/or increasing feed utilization and/or increasing egg yield, and/or decreasing mortality in the population of poultry and/or swine and/or dairy cow.

The advantages of the use of organic metal chelates is further supported by the fact that by selecting a good ligand, the additive will be also cheaper. The production of the composition is very cheap, thus providing a solid price advantage. They play a major role in the economical production as a preventive agent with their bacteriostatic/bactericide properties. They may be effective for recovering the balance of the intestinal flora, for the production thereof and for fighting the facultative pathogenic microorganisms that are risk for the health of the animals. In addition to the profit loss due to bad feed utilization and animal loss, the yearly cost for antibiotics of farms having infected populations is also very high. In some cases, the cost of compositions e.g. for combating swine dysentery in a given factory swine farm may exceed 70% of the cost of medicaments used. The cost of treatment is around 2-7.5 $/animal on average. This treatment may be replaced by the microelement organic metal chelate premix.

At the same time, the copper and zinc glycinate provided in organic form not only utilized better, but surprisingly have an inhibiting effect on the microorganisms. The organic bound microelement chelate compositions in combination with each other are effective for recovering the balance of the intestinal flora, for the production thereof and for fighting the facultative pathogenic microorganisms that are risk for the health of the animals. The organic chelate complexes may be effective for diseases with complicated etiology, such as swine colitis, which can be caused by several facultative pathogenic bacteria.

TABLE 1

Occurrence of pathogenic microorganisms in swine farming.

| Pathogen | Incidence alone (No. of cases) | Mixed incidence (No. of cases) | Total incidence (No. of cases) | Incidence frequency (%) |
| --- | --- | --- | --- | --- |
| B. pilosicoli | 21 | 23 | 44 | 39 |
| Atypic Brachyspira | 7 | 2 | 9 | 8 |
| Brachispyra hyodysenteriae | 6 | 3 | 9 | 8 |
| L. intracellularis | 3 | 10 | 13 | 12 |
| Salmonella spp. | 4 | 8 | 12 | 11 |
| Y. pseudotuberculosis | 4 | 13 | 17 | 15 |
| E. coli | 1 | 5 | 6 | 5 |
| Clostridium perfringens | 0 | 2 | 2 | 2 |

A significant factor in the mechanism of action of organic chelates is that they are capable to inhibit the proliferation of pathogenic bacteria within the intestinal tract, therefore allowing for the predominance of useful members of the normal intestinal flora. We have studied several types of mono-, di-, bis-glycinate, methionate, lysinate, maleinate, propionate, stearate, valerianate, butylate O-chelate and/or N-chelate compounds of microelements to examine their effects on the proliferation bacteria/fungi. In the course of determining the MIC value for the individual trace element chelates, we selected the most optimal combination with economic benefits, and the research was continued with a focus on how the interaction of the chelates affect the biological properties thereof. Further, a basic question of the microelement administration is how to prevent the interaction of the metal ions with the other components of the intestinal flora before absorption, and this can be achieved by providing a formulation currently under patent protection.

The microelements, such as iron, copper, zinc, play a central role in the metabolism of obligate and facultative aerobic microorganisms, but they are present in the environment in minute amounts. The low level of availability of iron in plants is mainly due to the low solubility of ferric oxyhydroxide polymers. Within the well oxidized plant parts the solubility of e.g. the iron is mainly dependent on $Fe(OH)_3$. The solubility constant of these compounds is very low, ($K_{sol}=10^{-38}$), therefore the concentration of $Fe^{3+}$ at pH 7 is $10^{-17}$, whereas the minimal concentration for allowing normal plant growth is $10^{-6}$ M [Neilands et al. (1987)]. It is the microelement acquisition strategy of the microbe flora of the given microenvironment that is responsible to resolve the above contradiction. In such environments, mostly those species can live or "dominate" that have well-built and highly effective iron acquisition and/or microelement acquisition mechanism. The plants use the help of microorganisms for these purposes.

The microorganisms can use three main mechanisms to solubilize the insoluble microelement and/or e.g. Fe(III)-oxides: protonation, reduction and chelate forming. Protonation results in the increase of the dissociation of e.g. the $Fe(OH)_3$ complexes by shifting the equilibrium constant (one unit of decrease in the pH results in a thousand-fold increase in the solubility of Fe(III) ions). It is obvious that this can only be used with some limitations in nature. Conversion of Fe(III) into Fe(II) on the same pH results in a significantly increased solubility. However, this process has steps with high energy demands.

Chelate forming, which is prevalent in the real world, takes place with the help of the so-called siderophores, mainly produced by microorganisms. In the case when the microelement is less available in the environment of the microorganisms, many organisms starts to produce low molecular weight metabolites, siderophores and partially outer membrane proteins that are characteristic to the species and has high affinity for e.g. $Fe^{3+}$ ion (the outer membrane proteins play a role in the recognition of the Fe—siderophore complex and the absorption of iron [Weger et al. (1986)]), these components dissolve the microelements from the minerals and organic compounds (such as transferrin, lactoferrin). Siderophores are small molecular weight, species specific, divalent ligand molecules that are mainly attach through the oxygen atom to the Fe(III) ion with six bonds on octaeder directions, and take up the Fe3+ ions from the environment in the form of chelates and transport them into the microbial cell [Neilands, J. B. (1981), Leong, J. (1986)]. The transport of microelements into the cell's cytosol is mediated by a specific membrane receptor as well as a transport system that recognizes the iron—siderophore complexes. Thus the siderophore production of microorganisms in the small intestine with slightly acidic, neutral or alkalic environment is an important and generic phenomenon that is necessary for their proliferation capability.

Professionals with expertise in feeding know from experience that animals fed with feed lacking trace element (Zn, Cu, Fe, Mn, etc.) are more easily get sick with gastrointestinal diseases. The disease cannot be abolished by the administration of trace elements, but the incidence of diseases with digestive origin is less with a balanced trace element supply.

The components of the normal intestinal flora are present in significant amount, about $10^9$-$10^{10}$ CFU/ml in the small intestine. These are in the most cases the beneficial *Lactobacillus, Bifidobacterium* species that produce mainly lactic acid and provide the slightly acidic pH, therefore they are not in need of producing siderophores. The so-called pathogenic microorganisms e.g. *E. coli, Salmonella, Clostridium, Brachyspira* are present in the healthy intestinal flora in less than a maximal amount of $10^5$ CFU/ml.

According to the recent literature, the equilibrium between the pathogenic and non-pathogenic microorganisms within the gastrointestinal system was attributed to the pH. There is an actual basis for this hypothesis, since the Lactobacilli propagate in the acidic pH range and produce acids, such as lactic acid. The pathogenic microorganisms propagate in the neutral or slightly alkalic range, where the members of the normal intestinal flora are not capable of reproduction. This finding about the pH is the basis for the decades long use of compositions containing probiotics, Lactobacilli in stock farming. It must be noted that the result of this treatment is varied, in some cases it is surprisingly effective, and in others it is completely ineffective.

We intend to provide a completely new surprising possibility compared to the recent state of the art for the treatment of digestive tract problems. The microelement chelates, due to their specific structure, have better absorption and utilization properties and are surprisingly capable to inhibit the propagation of facultative pathogenic microorganisms. The spectrum of the compounds useful for the treatment is broad. In the case of probiotics, several different microorganisms are used and the composition of the microorganisms used is varied according to the expected effect. Different microorganisms are used in the case of birds and others for swine. Based on our present finding, this is entirely warranted, since the composition of pathogenic microorganisms causing problems in the case of birds is different from the one for the swine.

We theorize that the so called siderophore chelate forming ligands play a major role in the formation of the ratio of the normal microflora and pathogenic microorganisms, which provide an advantage within the slightly alkalic or neutral environment of the small intestine for the siderophore producing pathogenic bacteria "hungry" for metal ions. Therefore, when the microelement chelates according to the invention are surprisingly attached to the bacterial siderophore binding membrane receptors, the pathogenic bacteria will not have the advantage with their microelement uptake and thus propagation.

The composition of the intestinal flora in the large intestine is completely different from that of the small intestine. Instead of the intestinal flora dominated by e.g. *Lactobacillus*, it has an intestinal flora dominated by e.g. *Clostridium*, i.e. it has a pathogenically dominated intestinal flora. It is known, however, that the absorption of the trace element occurs in the posterior segment of the small intestine. Based on this, we also theorize that the siderophore chelate forming factors that are complex compounds containing trace element or trace elements, provide exclusive advantage for the bacteria producing these siderophore ligands within the chronically inflamed large intestine—this is a frequent clinical state found in birds. It follows from the above finding that microelement compounds must be found that may inhibit the pathogenic, siderophore producing microorganisms present in the gastrointestinal tract, and composed of a combination trace elements and organic compounds. Further, if the effect for saturating the trace element containing siderophore receptor is real, then the small intestine needs to be searched for compounds that area capable to inhibit the propagation of pathogenic microorganisms in low concentration while affect the non-pathogenic but siderophore-producing *Enterococcus* forming the normal intestinal flora only in higher concentration.

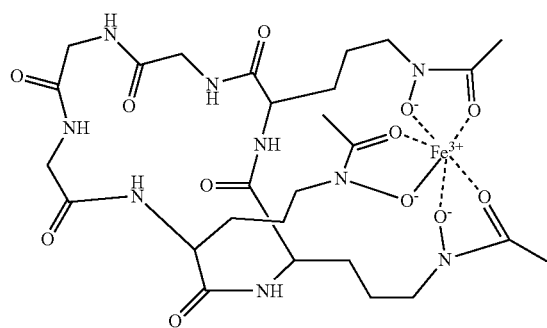

A

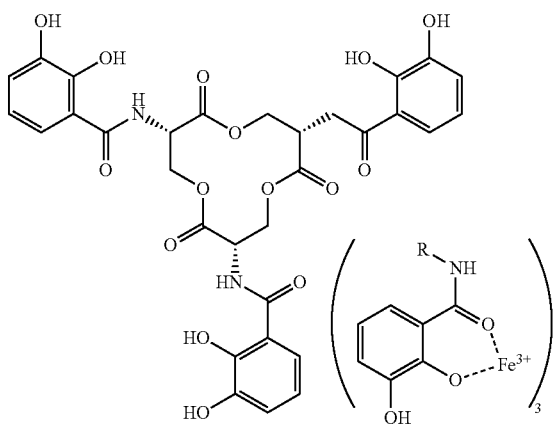

B

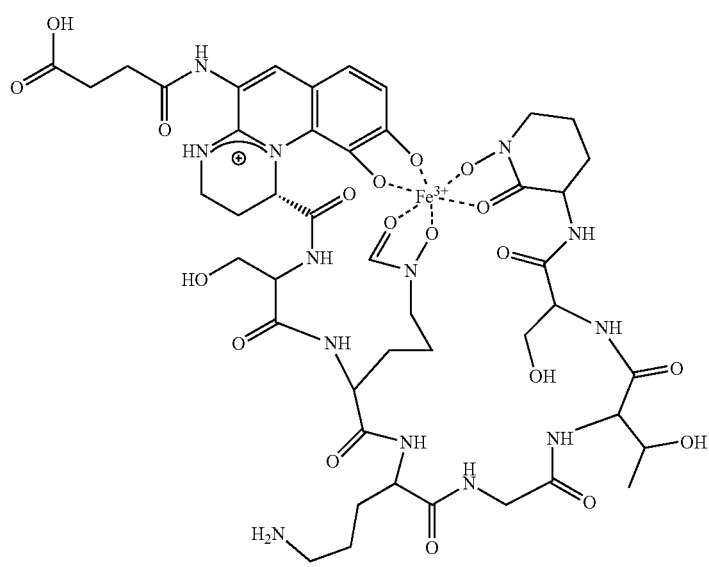

C

-continued

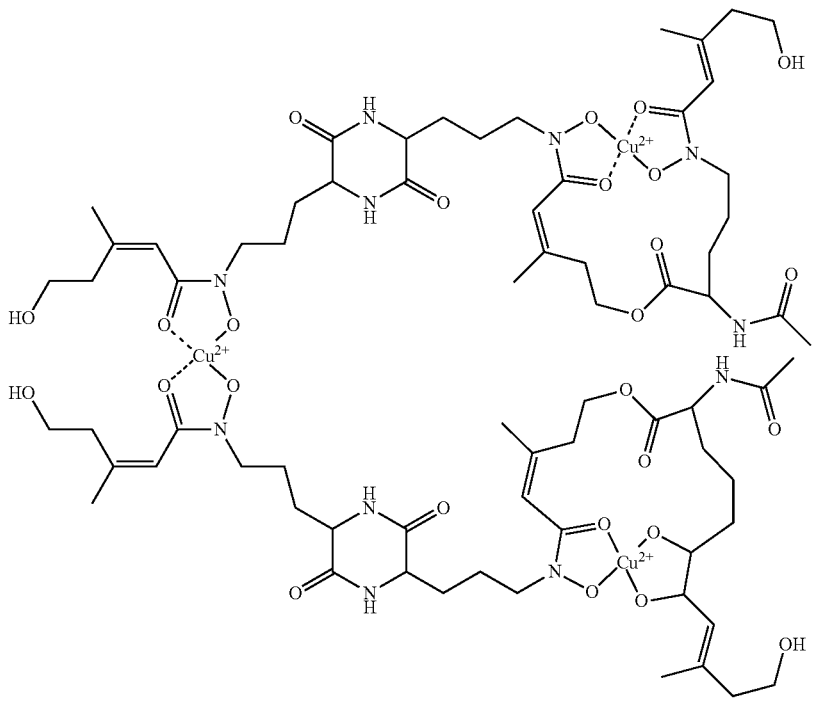

D

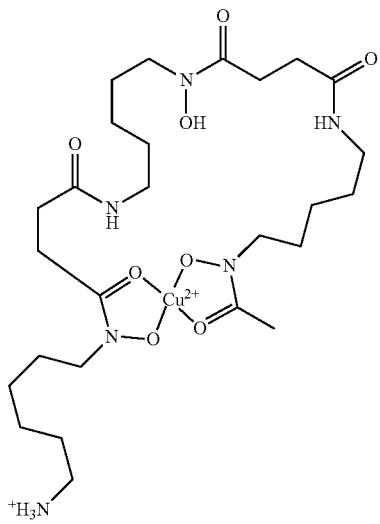

E

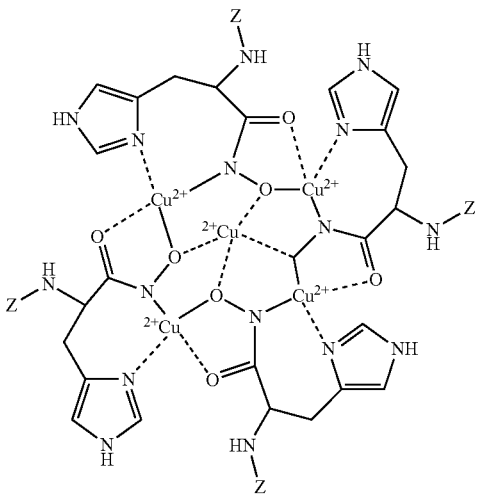

I

Structure of siderophores: types A, B and C of Fe siderophores and types D, E and I of copper siderophores.

A further effect is that the organic microelement chelate siderophore type ligand is coupled with an antibiotic molecule that inhibits the reproduction or cellular synthesis, therefore the pathogenic bacterium takes up it with its siderophore receptors. Thus more effective inhibitor and/or killing effect may be achieved with the antibiotic coupled to the organic chelate than with the antibiotic compound alone.

A further effect is that via the communication between the bacterial cells—quorum sensing (QS)—bacteria are capable to synchronize their genetic functions and produce certain compounds when proliferate in high numbers. This occurs when the bacteria reach an amount where they so called colonize and form a layer, "biofilm", for example on the surface of the intestine or on an area of a wound. This may also occur when if they are in sufficient numbers in the blood, reaching the farthest points in the organism under attack. The increase of the concentration of the secreted QS signal molecules is a signal for the bacteria to start intensive proliferation. The QS molecules are mainly long chain fatty acids, quinols, methyl esters of fatty acids, N-acyl homoserine compounds, and similarly to the siderophores, attach to specific receptors of the bacteria. According to our hypothesis, these receptors—similarly to the siderophores—may be a specifically saturated by the microelement organic chelate compounds, thus the QS signal molecules are unable to exert their effects. This prevents the communication between the bacteria and thus their proliferation, colonization and biofilm formation.

In our experiments, we studied compounds of mainly Zn, Cu, Mn and Fe as trace elements in organic bonds. We determined that the known trace element glycinates, trace element methionates, trace element malonates, etc. already used in the feed industry as a more effective trace element source have selective inhibitory effect on certain pathogenic microorganisms. The selectivity and biological activity may be enhanced by the combination of trace element chelates O- and N-chelates. A selective biological activity was achieved with amino acids, such methionine, lysine, glycine, etc., monovalent acids, such as acetic acid, propionic acid, butyric acid, isobutyric acid, etc., hydroxy acids, such as lactic acid, etc., dicarboxylic acids, maleic acid, polycarboxylic acids. With Zn, Cu, Mn and Fe salts of the above. Surprisingly, the microbiological activity significantly increases in the case of the formation of an O-chelate, preferably with a water molecule, or an N-chelate, preferably with ammonium.

The trace elements mentioned are so called chelate forming compounds, therefore we extended our studies for the N- and O-chelate compounds of the above trace elements that carry the biological effect.

Further, we prepared chelate compounds that, in addition to the above described N- and O-chelate formation, contain 0-6 ammonia or 0-6 water molecule in chelate bonds with the central metal ion.

The microelement glycinate chelates may be especially similar to the structure of the siderophores and thus by attaching to the siderophore receptor of the cell may prevent the microelement, such as iron utilization of the microorganisms and therefore the cell dies. Therefore the iron, zinc, copper, manganese—glycinate chelate complex due to its structure is capable to cover the membrane receptor of the bacterial cell, preferably with its specific affinity to the species-specific membrane receptor of the given bacterium cell directly influences the microelement supply and consequently the viability, reproduction, and thus preferably death of the cell. The effect depends on the receptor sensitivity of the given bacterium species, strains, therefore certain species or strains may be insensitive, consequently it can be stated that the effect of the microelement chelates is species-specific, and it requires a separate microbiological measurement for every bacterial group to achieve the appropriately effective MIC and/or preferably CID effect.

According to some studies, the developed microelement chelate, e.g. glycinate completely inhibited the proliferation of Gram positive microorganisms even in the presence of blood. Its inhibitory effect on the proliferation of *Pseudomonas* strains was weaker, and the effect was stronger on other Gram negative microorganisms, as well as on some fungus. The studies conducted so far with the different mocroelement chelate extracts clearly demonstrated their effectiveness on the most diverse pathogenic and food spoiling microorganisms. According to these studies, its activity on Gram positive bacteria is higher, than on Gram negatives, while in other compositions, we also found pronounced effect against Grain negatives under in vitro conditions.

In the case of necrotic *enteritidis* of birds (broiler chicken, egg laying hens, turkey) and acute swine dysentery, the number of enterococci and lactobacilli is significantly decreased in the intestinal flora, and at the same time, the number of fusobacteria, bacteria of the genus *Bacteroides*, *E. coli* and certain coliform bacteria, as well as Clostridiums is increased. In long lasting cases, an increase of clostridia is apparent. Due to all of these, our studies were conducted into this direction: according to our liquid culture and agar diffusion tests, the microelement glycinate chelate inhibits the growth of *Micrococcus luteus*, *E. coli*, *Salmonella enteritidis* and *Clostridium perfringens* strains either partially or completely. The minimal inhibitory or killing concentrations (MIC and CID) are measured in biological assays and determined for each strains.

By combining them with copper and zinc aminate chelate compounds we were able to enhance the bacterial inhibition capability. The optimal ratio of microelement chelate mixtures is determined in agar diffusion and liquid culture biological assays. When studying the effect of the metal chelate complexes from a microbiological viewpoint, we saw that when administered in certain concentrations, they are effective on the growth of some of the pathogenic microorganisms, while in the same concentration the reproduction of microbe population forming the normal intestinal flora is unharmed. Different antimicrobial effect can be measured when using different metal ions for the preparation of different metal chelate compounds. The Zn, Cu, Fe, Mn ions used to prepare the complex exert their effect on the microbes in different concentrations—even when we use the same ligand during the complex formation. During the experiments, we have found that the trace element chelates Zn and Cu glycinate in combination in vitro are useful for the prevention of enteral diseases caused by the examined *S. enterica* in double synergistic combination, and for the examined *C. perfringens* in triple synergistic combination, while selectively acting on the normal intestinal flora (e.g. Lactobacilli, *Saccharomyces*) prevent the proliferation of the facultative pathogenic microbes, while not inhibiting the lactic acid bacteria and yeast forming the normal intestinal flora. The pathogens *Clostridium barati*, *Cl. sordellii*, *botulinum* A-F, *Cl. novyy* A, B, C, D, *Cl. septicum*, *Cl. chuvoei*, *Cl. hystoliticum*, *C.*, *sporogenes*, *Cl. tetani* mainly causing superficial disease, are similarly sensitive to the copper and zinc organic chelate, preferably chelate aminate compounds.

Of course, the compounds according to the invention are equally suitable in human applications for the inhibition of the growth of the respective facultative pathogenic bacteria and for maintaining the beneficial elements of the intestinal flora, as well as for the treatment and prevention of diseases caused by such pathogenic bacteria.

EXAMPLE 1—PREPARATION OF ZINC BIS-GLYCINATE CHELATE

Figure 1:
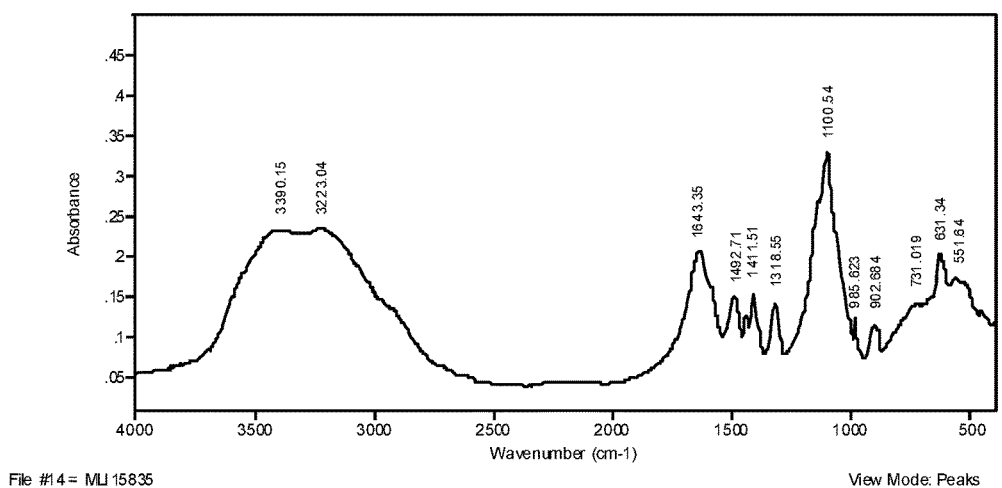
FIG. 1. IR spectrum of zinc mono-glycinate chelate.

To 1 mol ZnO (79.5 g), 200 nil distilled water, 2.1 mol $NH_4OH$, and 48.5 g $CO_2$ is added. The reaction product is $Zn(NH_4)_2CO_3$ at 120 C and 10-12 bar pressure, after 4 hours of reaction time. The pH of the obtained chelate compound is set with $CO_2$ to a value of 8.0. At this time, $ZnCO_3$ precipitate is formed. The precipitate obtained is filtered, then reacted with 2 mol glycine. This way, the following compound with structure (I) is formed:

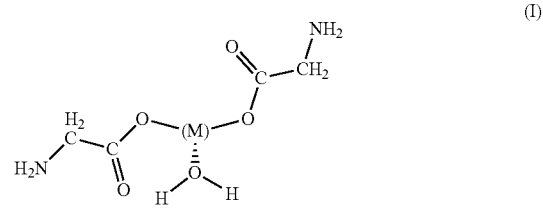

(M)(Glycine)$_2$, wherein M is Zn or Cu. A preferred example of the compound of formula is Zn(Glycine)$_2$.

The drying step for the preparation of the compound is preferably carried out so as to keep the water content of the microelement chelate compound by retaining the appropriate water content. In the case when the product is dried to a water content of 12-14%, a powder formulation of the compound of formula (I) is obtained. If the product dried to near zero, to about 3% water content, then it loses its water content connected to the central metal atom by dative bond. The biological activity of this latter product is different, it will be significantly lower than that of compound of formula (I). The product is a thick, hygroscopic, viscous compound that has high solubility in water.

EXAMPLE 2—PREPARATION OF ZINC DIAMMONIUM BIS-GLYCINATE CHELATE

To 1 mol ZnO (79.5 g), 150 ml distilled water, 2.2 mol NH$_4$OH, and 48.5 g CO$_2$ is added. The reaction product is Zn(NH$_4$)$_4$CO$_3$ at 120 C and 10-12 bar pressure, after 4 hours of reaction time. The obtained chelate compound is directly reacted with 2 mol glycine. The following compound with structure (II) is obtained:

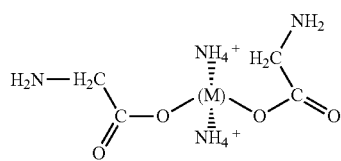

(II)

(M)(NH$_4$)$_2$(glycine)$_2$, wherein M is Zn or Cu. The glycine may be replaced by any amino acid, for example methionine, lysine, aspartic acid, etc. A preferred compound according to formula (II) is Zn(NH$_4$)$_2$(glycine)$_2$.

EXAMPLE 3—PREPARATION OF ZINC TETRAAMMONIUM BIS-GLYCINATE CHELATE

To 1 mol ZnO (79.5 g), 100 ml distilled water, 4.2 mol NH$_4$OH, and 48.5 g CO$_2$ is added. The reaction product is Zn(NH$_4$)$_4$CO$_3$ at 120 C and 10-12 bar pressure, after 4 hours of reaction time. The obtained chelate compound is directly reacted with 2 mol glycine. The following compound with structure (III) is obtained:

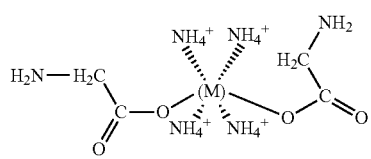

(III)

(M)(NH$_4$)$_4$(glycine)$_2$, wherein M is Zn, Cu or Fe. The glycine may be replaced by any amino acid, for example methionine, lysine, aspartic acid, etc. A preferred compound according to formula (III) Zn(NH$_4$)$_4$(glycine)$_2$.

EXAMPLE 4—PREPARATION OF ZINC MALATE CHELATE

To the ZnCO$_3$ compound prepared as described in Example 1, 2.0 mol malic acid is added in aqueous solution. The following compound with structure (IV) is obtained:

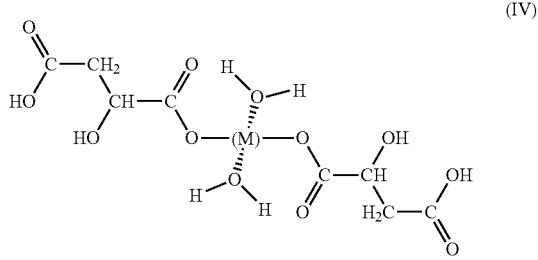

(IV)

Zn malate. The malic acid may be replaced by any hydroxy acid, for example glycolic acid, lactic acid, hydroxy-butyric acid, citric acid, etc. Zinc may be replaced with another trace element, for example copper, etc.

The drying step for the preparation of the compound is preferably carried out so as to keep the water content of the microelement chelate compound by retaining the appropriate water content. In the case when the product is dried to a water content of 10-12%, a powder formulation of the compound of formula (IV) is obtained. If the product dried to near zero, to about 3% water content, then it loses its water content connected to the central metal atom by dative bond. The biological activity of this latter product is different, it will be significantly lower than that of compound of formula (IV).

EXAMPLE 5—PREPARATION OF ZINC DIAMMONIUM MALATE CHELATE

To the Zn(NH$_4$)$_2$CO$_3$ compound prepared as described in Example 2, 2.0 mol malic acid is added in aqueous solution. The following compound is obtained:

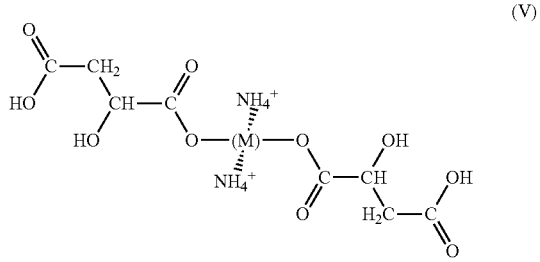

(V)

Zn diammonium malate. The malic acid may be replaced by any hydroxy acid, for example glycolic acid, lactic acid, hydroxy-butyric acid, citric acid, etc. Zinc may be replaced with another trace element, for example copper, etc.

EXAMPLE 6—PREPARATION OF ZINC TETRAAMMONIUM MALATE CHELATE

To the Zn(NH$_4$)$_4$CO$_3$ compound prepared as described in example 3, 2.0 mol malic acid added in aqueous solution. The following compound with structure (VI) is obtained:

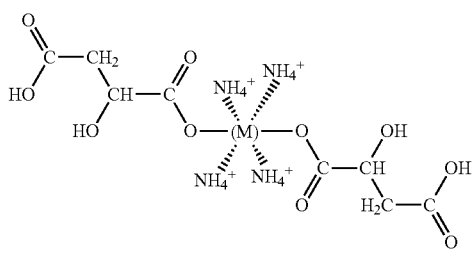

(VI)

Zn tetraammonium malate. The malic acid may be replaced by any hydroxy acid, for example glycolic acid, lactic acid, hydroxy-butyric acid, citric acid, etc. Zinc may be replaced with another trace element, for example copper, etc.

EXAMPLE 7—PREPARATION OF ZINC DIAMMONIUM METHIONATE CHELATE

To the $Zn(NH_4)_2CO_3$ compound prepared as described in Example 2, 2 mol methionine is added in aqueous solution.

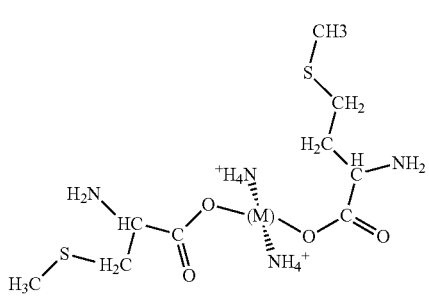

(VII)

Zn diammonium methionate.

EXAMPLE 8—PREPARATION OF ZINC DIAMMONIUM LYSINATE CHELATE

To 1 mol of the $Zn(NH_4)_2CO_3$ compound prepared as described in Example 2, 2 mol lysine is added.

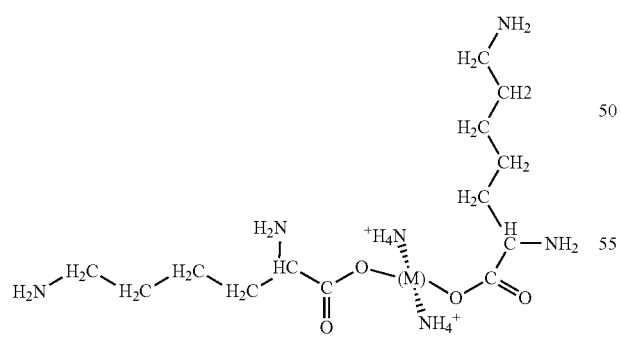

(VIII)

Zn diammonium lysinate.

EXAMPLE 9—PREPARATION OF TRACE ELEMENT AMINATE CHELATE

To 1 mol of the $ZnCO_3$ or $CuCO_3$ compound prepared as described in Example 1, 2 mol amino acid of choice is added. The compound obtained is $Zn(aminate)_2$ chelate.

In the case when the product is dried to a water content of 12-14%, then $Zn(H_2O)(aminate)_2$ is formed. If the product dried to near zero, about 3% water content, then it loses its water content connected to the central metal atom by dative bond. The biological activity of this latter product is different, it will be significantly lower than that of the compound $Zn(H_2O)(aminate)_2$ compound.

EXAMPLE 10—PREPARATION OF TRACE ELEMENT DIAMMONIUM CHELATE

To 1 mol of the $Zn(NH_4)_2CO_3$ compound prepared as described in Example 2, 2 mol amino acid of choice is added. The compound obtained is Zn diammonium aminate chelate.

EXAMPLE 11—PREPARATION OF TRACE ELEMENT EDTA CHELATE

To 1 mol of the $Zn(CO_3)$ compound prepared as described in Example 1, 1 mol EDTA is added in aqueous solution. After the completion of the reaction, the final product, preferably applied onto a carrier, is dried to 10% water content, to obtain the following O-chelate compound.

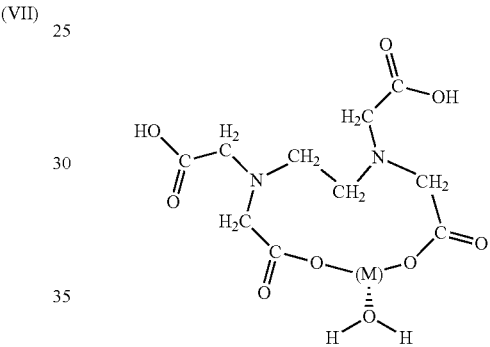

EXAMPLE 12—PREPARATION OF TRACE ELEMENT DIAMMONIUM EDTA CHELATE

One mole of the Zn(NH4)2CO3 compound prepared as described in Example 2 is reacted with 1 mol EDTA, to obtain the following compound. Zinc may be replaced with copper, iron or manganese as chelate forming trace element.

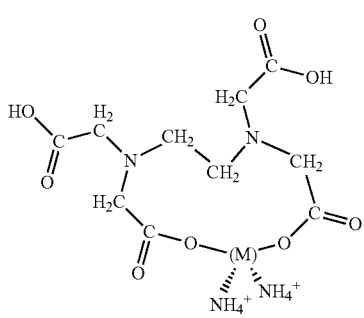

EXAMPLE 13—PREPARATION OF ZINC MONO-GLYCINATE CHELATE ON A FACTORY SCALE

We performed the preparation of a chelate in 8000 liter reactors and thus produced trace element chelate. To 4000 liter water, 2875 kg zinc sulfate heptahydrate and 750 kg glycine was added. After reacting for 4 hours at 90 C, a zinc mono-glycinate product is formed, that was converted to a micro-granulate in a fluid bed dryer, thus obtained the product.

The formation of chelate bonds in the product obtained were verified by structure determining techniques (complexometric metal ion analysis, calefaction experiments, acid-base titration, recording of central IR spectra) and by recording the far IR spectra of the obtained product. FIG. 1 shows the IR spectrum of the zinc mono-glycinate chelate. Evaluation of the IR spectrum:

2000-4000 cm$^{-1}$:

Two distinct bands appear with band maximums of 3160-3211 cm$^{-1}$ and 3456-3390 cm$^{-1}$, respectively. In the case of the latter bands, there is a shoulder in the higher wave number range. The previous band can be assigned to the NH valence vibrations of the NH$_3^+$ group (based on the spectrum of glycine, glycine. HCl). The latter band(s) can be assigned to the coordinated water molecules. The presence of the "shoulder" indicates that there are water molecules bound with varying strengths (e.g. coordinated and non-coordinated, bound by only hydrogen bridges).

Bands at 1600, 1400 cm$^{-1}$ and the proximity thereof:

In both cases, one sharp and intensive band maximum can be observed (1643, 1643, 1649, 1652, 1651 cm$^{-1}$) and (1412, 1411, 1410, 1409, 1410 cm$^{-1}$), respectively. This indicates that the carboxylate group of the glycine is coordinated in each case. The differences of the respective band maximums (231, 222, 239, 243, 241 cm$^{-1}$) indicates bidentate coordination, i.e. both oxygens are coordinated. A bridge type bond may be presumed, as it was suggested in the case of Cu(Glycine)SO$_4$x2H$_2$O, Zn(Glycine)SO$_4$x2H$_2$O complexes, based on X-ray diffraction data [3].

1500 cm$^{-1}$ and the proximity thereof:

In each samples, a medium intensity band may be observed with a maximum around 1500 cm$^{-1}$ (1492, 1480, 1478, 1478, 1476 cm$^{-1}$), which clearly indicates the presence of protonated glycine(NH$_3^+$), in accordance with what is observed in the 2000-4000 cm$^{-1}$ range.

1100, and 600 cm$^{-1}$, and the proximity thereof:

IN each samples, intensive bands may be observed near wave numbers 1100 and 600 cm$^{-1}$ (1100, 1081, 1108, 1113, 1113, 1114 and 631, 617, 618, 618, 617 cm$^{-1}$, respectively). At the same time, a shoulder may be observed at the higher wave number range, which indicates that the sulfate ion is coordinated to the metal ion as an ion or/and in monodentate manner (with a single oxygen).

In the place of glycine, any other amino acid may be present, such as methionine, lysine, aspartic acid, etc. Zinc may be replaced with another trace element, for example copper, manganese, etc.

EXAMPLE 14—PREPARATION OF COPPER MONO-GLYCINATE CHELATE ON A FACTORY SCALE

To 1.8 cubic meter water, 375 kg glycine was added at 60-70° C. To this solution, 1250 kg crystalline CuSO$_4$ is added while heating it to 80° C., then cooled for 30 minutes. The reaction product is dried into a micro-granulate in a fluid bed dryer.

Figure 2:
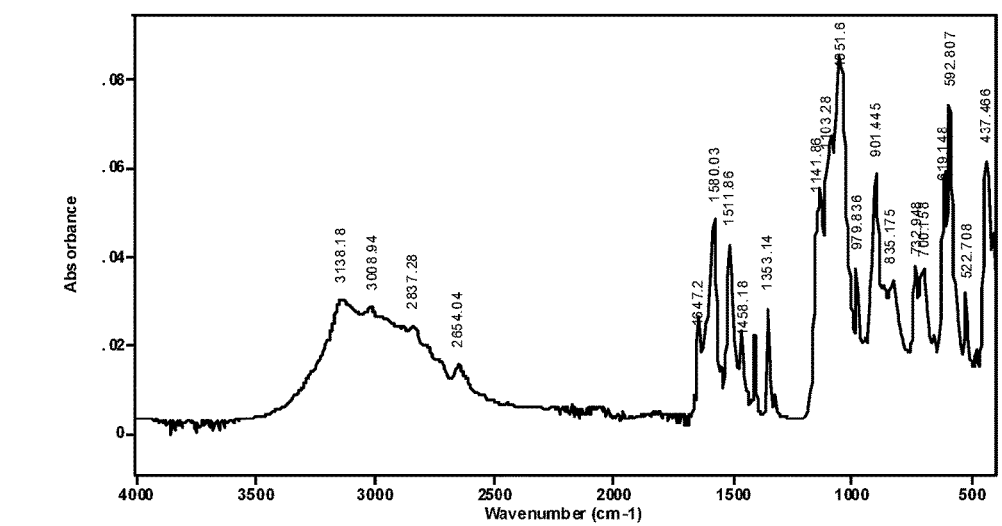
FIG. 2. IR spectrum of copper mono-glycinate chelate.

The Cu—chelate—glycine coordination of the factory product is clearly visible on the IR spectrum. The glycine molecule is coordinated through the carboxylic group, and the amino group remains protonated. The carboxylate group is coordinated as a bidentate bridge. Two types of glycine molecules are visible as coordinated in different environments. The glycine is coordinated through the carboxylic group, as a bidentate bridge ligand. The amino group of the glycine remains protonated. The sulfate ion is coordinated in monodentate and/or bidentate manner. FIG. 2 shows the IR spectrum of the copper mono-glycinate chelate.

2000-4000 cm$^{-1}$ band maximum is visible at wave numbers 3138 and 3192 cm$^{-1}$, respectively, with several smaller maximums in the lower wave number range.

1600, 1400 cm$^{-1}$ and the proximity thereof: 2 of each band maximums are visible, 1647, 1580 (in both cases) and 1458, 1410 and 1463, 1409 cm$^{-1}$ wave number values, respectively.

1500 cm$^{-1}$ and the proximity thereof: there is a medium intensity hand is visible at a value of 1512 and 1502 cm$^{-1}$, respectively.

1100 and 600 cm$^{-1}$ and the proximity thereof: there are 3 and 2 band maximums are visible, respectively, with shoulders.

Conclusion: the carboxylic group of glycine is coordinated, the amino group is protonated. The sulfate ion binds to the copper ion in bidentate manner.

EXAMPLE 15—PREPARATION OF A MIXTURE OF ZINC AND COPPER MONO-GLYCINATE CHELATE

A 1000 liters of the Zn mono-glycine chelate prepared in Example 11 is mixed together with 250 liters of the Cu mono-glycine chelate prepared in Example 12 at 60 C in a blade mixer reactor, then the thus obtained mixture is dried into a micro-granulate in fluid bed dryer.

EXAMPLE 16—DETERMINATION OF MIC AND CID CONCENTRATIONS OF MICROELEMENT CHELATE COMPOUNDS ON FACULTATIVE PATHOGEN MICROORGANISMS AND ON NORMAL COMPONENTS OF THE ENTERAL FLORA

The conventional methods for studying the antimicrobial activity—from a practical, curative medical viewpoint, the resistance spectrum of the antimicrobial agent—are the disk diffusion, or agar well diffusion assays, and dilution experiments done in liquid cultures. In a standardized (NCCLS, DIN, etc.) disk or hole diffusion assay, the effects of an antimicrobial agent is studied on the growth of a test microorganism spread onto the surface of an agar culture dish. In an agar diffusion assay e.g. a bacterial lawn is prepared on the agar dish, then according to the procedure developed in the laboratory, the inoculated plates are punched out in the middle with an agar disk cutting device. Then 10-100 μl assay sample is placed into the hole. The test compound diffuses from the test disk placed onto the bacterial lawn or from a hole made in the agar dish into the culture medium, and thus forms a growth-propagation inhibition zone around the disk or hole. Based on the agar diffusion test, the sensitivity of the strain studied can be unambiguously determined against the test compounds. According to the clinical practice, similarly to the standardized assays of antibiotic agents (where the diameter of the zone is proportional to the concentration of the agent), we classify according to the sensitivity zones formed around the disk holes. In the case of each agents, the microorganisms are qualified as resistant or sensitive to the given agent based on the zone diameter. The use of new antimicrobial agents requires high level of caution. Namely, it is not known what influences the diffusion of the antimicrobial agent (in the agar diffusion assay), such as the pH of the medium, the concentration of dissolved $O_2$ or $CO_2$, interactions with the components of the medium), therefore the appropriate techniques and mediums suitable for both the given agent and microorganisms must be selected based on multiple factors. Suitable concentrations of the microorganisms were prepared in liquid cultures in culture dilution tests, and the progress of growth and propagation was verified by microscope and/or optical techniques. This test allows the determination of the minimal inhibitory concentration (MIC) of the agent of interest on a given microorganism. Further, in the case when the death of the microorganisms within the tubes not showing growth is also checked, to determined whether the agent has only a static (growth inhibitor) or a cid (i.e. having microbe killing activity) effect, then the minimal cid concentration (MCC) may also be determined. The ratio of MCC/MIC gives an essential information on the in vivo efficacy of the agent: if this value is high, the in vivo usefulness of the agent is probably low.

TABLE 2

The strains examined in the study:

| | |
|---|---|
| Pathogen strains: | *Salmonella enterica* subp. *Enterica* serovar *enteritidis* (SALMO) |
| Facultative pathogen strains: | *Escherichia coli* ATCC 35218 (COLI) |
| | *Micrococcus luteus* NCAIM B 01072 (MCC) |
| | *Brachyspira hyodysenteriaea* (own isolate, B/06) |
| | *Staphylococcus aureus* NCAIM B.01065$^T$ |
| | *Streptococcus agalactiae* NCAIM B.01882$^T$ |
| | *Clostridium perfringens* NCAIM B.01417$^T$ |
| Components of the normal enteral flora, lactic acid producers: | *Lactococcus lactis* subsp. *Lactis* NCAIM B 02070$^T$ |
| | *Lactobacillus casei* v. *rhamnosus* Döderlein LCR 35 |
| | *Leuconostoc mesenteroides* (LACTIC ACID PRODUCERS) |
| Fungi: | *Saccharomyces cerevisiae* (LSE) |

Until using in the assays, the strains were stored in suspended form in TSB broth (Scharlau Microbiology) with 25% sterile glycerol frozen at −80° C. or lyophilized.

Isolation of *B. hyodysenteriaea* Strain (B/06)

*B. hyodysenteriae* strains were isolated from growing and store-pigs showing the clinical symptoms of swine dysentery, raised in different regions of Hungary. After slaughtering at the slaughterhouse, the colon snares of the pigs showing clinical signs were tied down and were transported to the laboratory within six hours. After opening the colon sections, the sample was provided as scraping from the colon mucosa. In every case, the mucosal scrapings on a streaker were spread onto the surface of freshly prepared TSA (tryptone-soy) agar (Scharlau Microbiology) supplemented with 10% defibrinated bovine blood and 400 µg/ml spectinomycin (Sigma-Aldrich Kft.). After inoculation, the cultures were incubated for 96 hours at 42° C. under strictly anaerobic conditions. The anaerobic conditions were achieved by using anaerobic gas generating pouches (Oxoid, Gas Generating Kit, Anaerobic system BR0038B) and anaerobic culturing jars (Oxoid, Anaerobic jar). The determination of the primary and secondary biochemical properties and the identification of the isolated strains was carried out by standard techniques (Quinn et al., 1994).

In Vitro Inhibition Experiments

Addition of a given amount (ppm, mg/kg, µg/ml) of trace element to the microbial culture medium from stock solution. The sample solutions with varying compositions were 2× serially diluted in liquid culture medium on a 24-well Greiner tissue culture plate, then 5 µl suspension of the sample bacterium in 0.5 MacFarland density prepared with physiological saline was measured into the different concentration liquid culture mediums. In the case of assaying combinations of active ingredients, a cross dilution technique was used, when the two different solutions were diluted across the surface of the plate from two directions. The plates were incubated for 24 hours at the atmospheric conditions required by the bacterium assayed. The results were then read, and the Minimal Inhibitory Concentration (MIC) of the test compounds was thus determined. In the cases where the Minimal Lethal concentration (CID) was assayed, then from the wells not showing opacity after the incubation period, 10 µl solution was inoculated onto the surface of blood agar and checked whether any bacterial growth occurred on the surface of the culture medium after the incubation period.

Agar Gel Diffusion

*Clostridium perfringens*: The strain grown in aerobic or anaerobic vessel was propagated on sterile agar, from which a suspension with 0.5 MacFarland density was prepared with sterile physiological saline, then inoculated onto the surface of culture media with cotton swabs. A hole was welled into inoculated media with specialized puncturing tool, then 50 µl of the test solution of the microelement chelate complex in varying concentrations were measured into the holes. Evaluation of the cultures was carried out by visual inspection. The presence of an inhibition zone formed around the holes is indicative of the efficacy of the tested solution.

*B. hyodysenteriae* (B/06): In these assays, precultures were prepared from the thawed bacterial mass on blood agar (modified tryptone soy agar, supplemented with 5-10% defibrinated bovine blood). From the visibly well-hemolyzed preculture agar plates, 8-10, nearly same sized (±5% difference) agar block inoculates were excised, then were spread onto 90 mm diameter freshly prepared agar plates with a sterile glass rod with rounded end about 5 mm in diameter. The plates were dried in covered form for 5 minutes.

According to the procedure developed in the laboratory, the inoculated plates were punched out in the middle with an agar disk cutting device. 100 µl of the given dilution of the test compound was placed into the hole with 5 mm diameter. After dripping the solution with known concentration, the plates were placed into an anaerostat (Oxoid anaerobic pouch and jar) within 15 minutes, and incubated at 37° C. for 4-5 days in oxygen free atmosphere.

Figure 3:
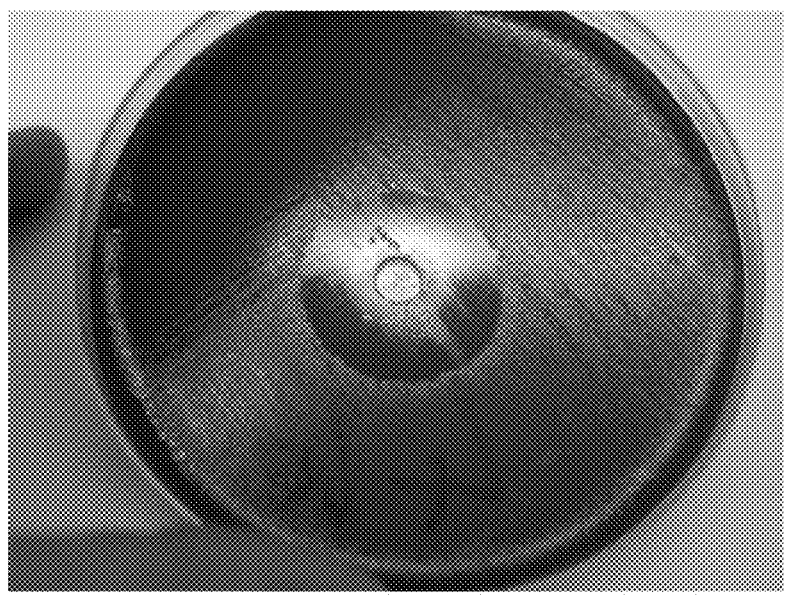
FIG. 3. *Clostridium perfringens* forms an inhibition zone on TSA agar medium.

The bacterial culture of *Clostridium perfringens* is inhibited by the microelement organic chelate placed into the hole at the middle of the agar dish. The compound diffused into the agar forms a well-defined, concentrically shaped inhibition zone depending on the concentration, and due to the effect of dilution, the inhibitory effect ceases after a certain distance and the culture shows growth beyond the inhibition zone (see FIG. 3).

Determination of the CID Value

It is the concentration of the active ingredient that causes the complete death of the microbes. Under sterile conditions within a laminar box, a dilution series was prepared from the liquid culture mediums that were incubated for 24 hours, then from the dilution series 100 µl each was placed onto agar dishes and spread with a sterile glass rod. The incubation period is 24 hours under conditions favorable for the growth of the microbe, then the number of colonies on the agar dishes are counted.

Two options were taken into consideration for the evaluation
1. No colonies are visible on the agar dishes.
2. There are visible colonies on the agar dishes making the counting possible.

In the case where no colonies are visible on the culture medium after the incubation, it indicates the microbe killing effect (CID) of the trace element chelate. The number of countable colonies grown on the agar dishes gives the actual MIC value of the given trace element chelate.

EXAMPLE 17—MICROBIOLOGICAL MIC AND CID RESULTS OF MICROELEMENT (ZINC, COPPER, IRON, MANGANESE) CHELATE (MONO-, DI-, AND BIS-AMINATE, FATTY ACID, AND HYDROXY FATTY ACID, POLYAMINO CARBOXYLIC ACID) COMPOUNDS

The microbiological assay system showed biological activity at different concentrations with the microelement chelate complex samples studied.

It can be seen from the results of the experiments performed that the assay samples have different MIC values. The pathogens and facultative pathogens examined have significantly higher sensitivity than that of the components of the normal intestinal flora, fungi and lactic acid producers. It can be concluded from the in vitro results that mixing these test compounds into the feed would be preventive, it prevents the growth of pathogens and facultative pathogens, in addition to keeping the equilibrium. It was determined that the chelate compounds studied have different MIC values.

TABLE 3

Minimal inhibitory concentration (MIC) of the microelement chelate compounds in ppm (mg/kg).

| Assayed chelates | *Micrococcus luteus* | *Escherichia coli* | *Salmonella enterica* | LACTIC ACID PRODUCERS | *Saccharomyces cerevisiae* |
|---|---|---|---|---|---|
| Zinc mono-glycinate | 60 | 100 | 100 | 800 | 800 |
| Zinc di-glycinate | 60 | 100 | 120 | 800 | 800 |
| Zinc bis-glycinate | 440 | 360 | 320 | 800 | 800 |
| Zinc (H2O) bis-glycinate | 60 | 120 | 220 | 800 | 500 |
| Copper mono-glycinate | 200 | 400 | 400 | 800 | 800 |
| Copper di-glycinate | 200 | 340 | 450 | 800 | 800 |
| Copper bis-glycinate | 280 | 500 | 600 | 800 | 800 |
| Copper (H2O) bis-glycinate | 60 | 300 | 400 | 800 | 800 |
| Iron mono-glycinate | 100 | 350 | 450 | 1000 | 1000 |
| Manganese mono-glycinate | 100 | 300 | 300 | 1000 | 1000 |
| Zn diammonium bis-maleinate | NA | 80 | 120 | 500 | 500 |
| Zn bis-maleinate | NA | 280 | 360 | 600 | 600 |
| Zn(H2O)-bis-maleinate | NA | 90 | 120 | 500 | 600 |
| Cu diammonium bis-maleinate | NA | 262 | 262 | NA | NA |
| Zn diammonium bis-glycinate | NA | 115 | 115 | NA | NA |
| Zn tetraammonium bis-glycinate | NA | 140 | 140 | NA | NA |
| Zn($H_2O$) bis-alaninate | NA | 100 | 110 | NA | NA |
| Zn($H_2O$) bis-propionate | NA | 160 | 160 | NA | NA |
| Zn($H_2O$) bis-valerianate | NA | 120 | 120 | NA | NA |
| Zn($H_2O$) bis-butyrate | NA | 110 | 110 | NA | NA |
| Zn bis-salycilate | n.a. | >4000 | >4000 | n.v | n.a. |
| Zn bis-benzoate | n.a. | >4000 | >4000 | n.v | n.a. |
| Zn nitrolotriacetate | n.a. | 40 | 40 | n.v | n.a. |
| Cu($H_2O$) bis-maleinate | n.a. | 120 | 210 | n.a. | n.a. |
| Zn diammonium aspartate | n.a. | 92 | 184 | n.a. | n.a. |
| Zn diammonium bis-aspartate | n.a. | 123 | 247 | n.a. | n.a. |
| Zn diammonium tri-aspartate | n.a. | 114 | 228 | n.a. | n.a. |
| Zn mono-aspartate | n.a. | 74 | 74 | n.a. | n.a. |
| Zn($H_2O$) bis-aspartate | n.a. | 103 | 103 | n.a. | n.a. |
| Zn($H_2O$) tri-aspartate | n.a. | 75 | 70 | n.a. | n.a. |

TABLE 3-continued

Minimal inhibitory concentration (MIC) of the microelement chelate compounds in ppm (mg/kg).

| | | | | | |
|---|---|---|---|---|---|
| Zn diammonium glutamate | n.a. | 167 | 83 | n.a. | n.a. |
| Zn diammonium bis-glutamate | n.a. | 123 | 123 | n.a. | n.a. |
| Zn diammonium tri-glutamate | n.a. | 117 | 117 | n.a. | n.a. |
| Zn mono-glutamate | n.a. | 70 | 115 | n.a. | n.a. |
| Zn(H$_2$O) bis-glutamate | n.a. | 82 | 82 | n.a. | n.a. |
| Zn(H$_2$O) tri-glutamate | n.a. | 70 | 280 | n.a. | n.a. |
| Zn diammonium bis-histidinate | n.a. | >4000 | >4000 | n.a. | n.a. |
| Zn bis-histidinate | n.a. | >4000 | >4000 | n.a. | n.a. |
| Cu diammonium asparaginate | n.a. | 620 | 620 | n.a. | n.a. |
| Cu diammonium bis-asparaginate | n.a. | 1025 | 2050 | n.a. | n.a. |
| Cu diammonium tri-asparaginate | n.a. | 1400 | >4000 | n.a. | n.a. |
| Cu diammonium glutamate | n.a. | 688 | 343 | n.a. | n.a. |
| Cu diammonium bis-glutamate | n.a. | 775 | 775 | n.a. | n.a. |
| Cu diammonium tri-glutamate | n.a. | 1950 | 1950 | n.a. | n.a. |
| Zn diammonium citrate | n.a. | 48 | 98 | n.a. | n.a. |

| | *Staphylococcus aureus* | *Streptococcus agalactiae* | *Clostridium perfringens* | *Brachyspira hyodysenteriae* | *Arcanobacterium piogenes* |
|---|---|---|---|---|---|
| Zn diammonium bis-maleinate | 80 | 20 | 340 | 2315 | 21 |
| Zn(H$_2$O) bis-maleinate | 160 | 180 | 360 | 4400 | n.a. |
| Cu(H$_2$O) bis-maleinate | NA | NA | 50 | 88 | n.a. |
| Cu diammonium (maleinate)$_2$ | 262 | 131 | 65 | 143 | n.a. |
| Cu mono-glycinate | n.a. | NA | 50 | 90 | 92 |
| Cu di-glycinate | 2 | 145 | 50 | n.a. | n.a. |
| Cu bis-glycinate | 110 | 420 | 360 | 320 | 260 |
| Cu(H2O) bis-glycinate | 5.3 | 171 | 100 | 96 | 32 |
| Zinc mono-glycinate | 40 | 80 | 210 | >4000 | n.a. |
| Zn ethylenediamine-tetraacetic acid | n.a. | n.a. | 1000 | 450 | n.a. |
| Zn (H$_2$O)$_2$-ethylenediamine tetraacetic acid | n.a. | n.a. | 400 | 320 | n.a. |
| Cu(H$_2$O)$_2$-ethylenediamine tetraacetic acid | n.a. | n.a. | 60 | 100 | n.a. |
| Cu nitrolo triacetic acid | n.a. | n.a. | >4000 | 450 | n.a. |
| Cu ethylenediamine tetraacetic acid | n.a. | n.a. | 160 | 320 | n.a. |
| Zn diaminonitrolo triacetic acid | n.a. | n.a. | 400 | 600 | n.a. |
| Zn diamino ethylenediamine tetraacetic acid | n.a. | n.a. | 100 | >4000 | n.a. |
| Cu diaminonitrolo triacetic acid | n.a. | n.a. | 120 | 200 | n.a. |

TABLE 3-continued

Minimal inhibitory concentration (MIC) of the microelement chelate compounds in ppm (mg/kg).

| | | | | | |
|---|---|---|---|---|---|
| Cu diamino ethylenediamine tetraacetic acid | n.a. | n.a. | 20 | 80 | n.a. |
| $Zn(H_2O)$ bis-alaninate | n.v | n.v | >4000 | >4000 | n.a. |
| Zn bis-salycilate | n.v | n.v | >4000 | n.v | n.a. |
| Zn bis-benzoate | n.v | n.v | >4000 | n.v | n.a. |
| Zn mono-glycinate | 20 | 40 | 210 | >4000 | n.a. |
| Zn di-glycinate | 20 | 20 | 165 | >4000 | n.a. |
| $Zn(H_2O)$ bis-glycine | 4 | 29 | 180 | >4000 | n.a. |
| $Cu(H_2O)$ bis-maleinate | n.a. | n.a. | 50 | 88 | n.a. |
| Zn diammonium asparaginate | 46 | 23 | 369 | n.a. | n.a. |
| Zn diammonium bis-asparaginate | 62 | 15 | 494 | n.a. | n.a. |
| Zn diammonium tri-asparaginate | 114 | 14 | 456 | n.a. | n.a. |
| Zn asparaginate | 18 | 37 | 297 | n.a. | n.a. |
| Zn bis-asparaginate | 26 | 51 | 412 | n.a. | n.a. |
| Zn tri-asparaginate | 18 | 19 | 450 | n.a. | n.a. |
| Zn diammonium glutamate | 61 | 15 | 245 | n.a. | n.a. |
| Zn diammonium bis-glutamate | 42 | 21 | 334 | n.a. | n.a. |
| Zn triammonium tri-glutamate | 58 | 15 | 469 | n.a. | n.v |
| Zn glutamate | 36 | 18 | 475 | n.a. | n.a. |
| $Zn(H_2O)$ bis-glutamate | 21 | 10 | 331 | n.a. | n.a. |
| $Zn(H_2O)$ tri-glutamate | 35 | 17 | 281 | n.a. | n.a. |
| Zn diammonium bis-histidinate | >4000 | 12 | 1950 | n.a. | n.a. |
| Zn bis-histidinate | >4000 | 4 | 650 | n.a. | n.a. |
| Cu diammonium asparaginate | 620 | 20 | 38 | n.a. | n.a. |
| Cu diammonium bis-asparaginate | 1025 | 16 | 32 | n.a. | n.a. |
| Cu diammonium tri-asparaginate | 1400 | 43 | 44 | n.a. | n.a. |
| Cu diammonium glutamate | 343 | 11 | 43 | n.a. | n.a. |
| Cu diammonium bis-glutamate | 387 | 24 | 97 | n.a. | n.a. |
| Cu diammonium tri-glutamate | 487 | 8 | 30 | n.a. | n.a. |
| Zn diammonium citrate | 49 | 49 | n.a. | n.a. | n.a. |
| Ag glycinate | n.v | n.v | n.v | n.v | 184 |

Several conclusions can be drawn from the above results. Then minimal inhibitory concentration (MIC) of the microelement chelate compounds studied was determined for one or more facultative pathogenic microorganisms. It was determined that without exception, all was capable of inhibiting the pathogen microorganism. In concentrations of 60-200 ppm *Micrococcus luteus*, and/or in concentrations of 70-400 ppm *Escherichia coli*, and/or in concentrations of 80-488 ppm *Salmonella enterica*, and/or in concentrations of 40-498 ppm *Staphylococcus aureus*, and/or in concentrations of 10-427 ppm *Streptococcus agalactiae*, and/or in concentrations of 65-167 ppm *Clostridium perfringens*, and/or in concentrations of 90-494 ppm *Brachyspira hyodysenteriae*, and/or in concentrations of 21-184 ppm *Arcanobacterium piogenes* was inhibited.

The components of the normal intestinal flora, lactic acid producers *Lactococcus lactis* subsp. *Lactis, Lactobacillus casei v. rhamnosus* and *Leuconostoc mesenteroide* and/or *Saccharomyces cerevisiae* (LSE) were only inhibited at or above a concentration of 500 ppm, and preferably at concentrations of 800-1000 ppm.

EXAMPLE 18—DOUBLE SYNERGISTIC EXAMINATION OF MICROELEMENT (ZINC, COPPER, IRON, MANGANESE) MONO-GLYCINATE CHELATES. SYNERGIC STUDIES OF THE MICROELEMENT COMPONENT

There is a synergy between two or more test compounds when the biological effects thereof is enhanced by their interactions. Knowing the MIC and CID values, it was deemed important to ensure the selectivity of the trace element chelates. To achieve this goal, the experiments were continued with studying the microelement chelates together, looking for synergies.

TABLE 4

Compositions without showing synergy and antagonistic
Double synergistic MIC values (ppm) of microelement chelates

| Chelates assayed in double synergy | Clostridium | LSE and Lactococcus | E. coli inhibitory effect on each other | Salmonella inhibitory effect on each other | Brachyspira hyodysenteriae |
|---|---|---|---|---|---|
| Zn:Cu mono-glycinate | Zn 360:Cu 50 | Zn 800:Cu 800 | — | — | Zn 43,7:Cu22 |
| Zn:Fe mono-glycinate | Zn 350:Fe 1000 | Zn 800:Fe 1000 | Zn 180:Fe 110 | — | |
| Fe:Mn mono-glycinate | Fe 1000:Mn 500 | Fe 1000:Mn 1000 | — | — | |
| Zn:Mn mono-glycinate | Zn 350:Mn 500 | Zn 800:Mn 1000 | Zn 10:Mn 1940 | Zn 10:Mn 1940 | |
| Cu:Mn mono-glycinate | Cu 100:Mn 500 | Cu 800:Mn 1000 | — | — | |
| Cu:Fe mono-glycinate | Cu 100:Fe 1000 | Cu 800:Mn 1000 | — | — | |
| Zn maleinate - Cu mono-glycinate | Zn 90:Cu 23 | | | Zn 90:Cu 23 | |

TABLE 5

Compositions showing synergy
Double synergistic MIC values (ppm) of microelement chelates

| Chelates assayed in double synergy | E. coli | Salmonella |
|---|---|---|
| Zn:Cu mono-glycinate | Zn 90:Cu 50 | Zn 90:Cu 50 |
| Zn:Fe mono-glycinate | | Zn 30:Fe 260 |
| Fe:Mn mono-glycinate | Fe 250:Mn 240 | Fe 230:Mn 240 |
| Zn:Mn mono-glycinate | | |
| Cu:Mn mono-glycinate | Cu 210:Mn 240 | Cu 210:Mn 240 |
| Cu:Fe mono-glycinate | Cu 50:Fe 230 | Cu 50:Fe 230 |

Based on these results, the minimal inhibitory concentration (MIC) of 6 trace element chelate was determined for the pathogenic *Salmonella enteritidis*. These trace element chelate concentrations have practically no effect on the normal components of the intestinal flora (LSE and *Lactococcus*) (800 ppm). In the case of the facultative pathogenic *E. coli*, however, five different compositions of these six trace element chelate have effective synergistic MIC value.

EXAMPLE 19—MULTIPLE SYNERGISTIC EXAMINATION OF MICROELEMENT (ZINC, COPPER) AND ANION (AMINO ACIDS, ORGANIC AND HYDROXY ACIDS, ETC.) CHELATES

In addition to what was shown in Example 18, synergy was not only found when the microelements were combined, but synergies were recognizable when the anion part of the compounds, i.e. the amino acids, acids were combined (Table 5).

It was concluded based on the data of the table that a synergy exists beyond the base compounds if the chelate compounds consisting different metals are optimally mixed, as well as the anion parts are optimally mixed, and an aggregate effect can be obtained if chelates comprising $NH_4^+$, $H_2O$ ligands are mixed.

TABLE 6

Compositions showing sextuple synergy

| Synergy of aminates | Escherichia coli | Salmonella enteritidis | Staphylococcus aureus | Streptococcus agalactiae | Clostridium perfringens |
|---|---|---|---|---|---|
| Zn animate$_6$ (gly$_2$, asp$_2$, glu$_2$, his$_2$, lys$_2$, ala$_2$) | 195 ppm | 97 | 49 | 97 | 390 |
| Zn(NH4)$_2$ animate$_6$ (gly$_2$, asp$_2$, glu$_2$, his$_2$, lys$_2$, ala$_2$) | 75 | 150 | 37 | 78 | 298 |
| Cu (NH4)$_2$ animate$_6$ (gly$_2$, asp$_2$, glu$_2$, his$_2$, lys$_2$, ala$_2$) | 29 | 117 | 15 | 30 | 117 |

Explanation:
The trace element anionic chelates with the synergy of zinc ammonium carbonate aminates gly (glycine), asp (aspartic acid), glu (glutamic acid), his (histidine), lys (lysine) and ala (alanine) sextuple combination in concentrations of 49-390 ppm, the trace element anionic chelate zinc aminates also in sextuple synergy at concentrations 37-238 ppm and the copper ammonium aminates in sextuple synergy at concentrations of 15-117 ppm are useful in vitro to prevent the possible diseases caused by *E. coli* and *Salmonella enteritidis, Staphylococcus aureus, Streptococcus agalactiae* and *Clostridium perfringens* by interfering with the proliferation of the facultative pathogenic microbes.

EXAMPLE 20—MULTIPLE SYNERGISTIC EXAMINATION OF MICROELEMENT (ZINC, COPPER, IRON) MONO-GLYCINATE CHELATES. SYNERGIC STUDIES OF THE MICROELEMENT COMPONENT

Knowing that the double synergies of the trace element chelates gave 50-80% results on the proliferation of microbes, further triple synergy studies were carried out. Next to the trace element chelates in the double synergies, a third trace element chelate was added. For the determination of triple synergy, all assay methods were utilized, and the final results obtained is shown when the two liquid as well as the microplate assay gave the same result.

TABLE 7

Compositions without showing triple synergy
Triple synergistic MIC values (ppm) of microelement chelates

| Triple synergy variations | E. coli | Salmonella | Clostridium |
|---|---|---|---|
| | Zn mono-glycinate:Cu mono-glycinate:Fe mono-glycinate | | |
| 1 | Zn 20:Cu 100:Fe 20 | Zn 90:Cu 100:Fe 60 | — |
| 2 | Zn 90:Cu 10:Fe 40 | Zn 20:Cu 110:Fe 140 | — |
| 3 | Zn 10:Cu 60:Fe 260 | — | — |

TABLE 8

Compositions showing triple synergy
Triple synergistic MIC values (ppm) of microelement chelates

| Triple synergy variations | Coli | Salmonella | Clostridium |
|---|---|---|---|
| | Zn mono-glycinate:Cu mono-glycinate:Fe-glycinate | | |
| 1 | — | — | Zn 40:Cu 30:Fe 70 |
| 2 | — | — | Zn 40:Cu 30:Fe 20 |

The trace element chelates are useful in vitro for the prevention of enteral diseases caused by the examined *E. coli* and *Salmonella* in double synergistic combination, and for the examined *Clostridium* microbes in triple synergistic combination, by selectively prohibiting the proliferation of the facultative pathogenic microbes, while not inhibiting the lactic acid bacteria and yeast forming the normal intestinal flora.

EXAMPLE 21—DETERMINATION OF THE EFFECTIVE CID OR STATIC CONCENTRATIONS OF MICROELEMENT (ZINC, COPPER, IRON, MANGANESE) MONO-GLYCINATE CHELATES

The minimal lethal concentration (CID) is determined as described in Example 14.

TABLE 9

| COLI | | SALMO | | LACTIC ACID PRODUCERS | | LSE | |
|---|---|---|---|---|---|---|---|
| Fe 318 ppm | Zn 70 | Fe 318 ppm | Zn 70 | Fe 318 ppm | Zn 70 | Fe 318 ppm | Zn 70 |
| Cu 206 | Mn 242 | Cu 206 | Mn 242 | Cu 206 | Mn 242 | Cu 206 | Mn 242 |
| Cu 52 | Zn 88 | Cu 52 | Zn 88 | Cu 52 | Zn 88 | Cu 52 | Zn 88 |

| CID concentrations of different microelement chelates (ppm) | | | | | |
|---|---|---|---|---|---|
| Microelement chelates | Salmonella | S. tiphy | Clostridium | Lactococcus | LSE |
| Zinc mono-glycinate | 3000 | 3000 | — | 800 | 800 |
| Copper mono-glycinate | — | — | 200 | 800 | 800 |

In the case of *Salmonella* strains, the CID value of the zinc chelate is 30-fold higher than the MIC value, whereas in the case of *Clostridium* strains, the CID value of the copper chelate is only twice as much as the MIC value. This difference may also be explained with the different sensitivity of the microbe species. However, it should be considered in the case of the components of the normal intestinal flora that both chelate have the same concentration for the MIC and CID values, the results are being indicative of that in the case of the components of the normal intestinal flora, the proliferation of the microbe is not inhibited at these concentrations, but the microbes are killed.

EXAMPLE 22—PILOT FEEDING EXPERIMENTS WITH A COMPOSITION CONTAINING ZINC $(H_2O)_2$ ETHYLENEDIAMINE TETRAACETIC ACID AND COPPER $(H_2O)_2$ ETHYLENEDIAMINE TETRAACETIC ACID CHELATES IN COMBINATION

Experimental feeding was performed with growing pigs on two occasion, under pilot environmental conditions on a stock carrying *Brachyspira hyodysenteriae*.

The control and experimental groups both were comprised of 100 store-pigs. The latter group received the experimental composition, in the 1 kg/ton feed dose as determined in laboratory tests. In the first study, the control group received a preventive dose of an antibiotic in its feed (Table 10). In the second study, only the pigs suffering from dysentery were individually treated (Table 11). The parameters studied: number of treatments, development of losses, average slaughter weight, and feed utilization.

TABLE 10

Effect of the composition on the yield and health of store-pigs (The control group received preventive antibiotic treatment)

| Designation | Control group (antibiotic) | Experimental Group |
|---|---|---|
| Number of animals | 100 | 100 |
| Initial average weight (kg) | 31.5 | 31.7 |
| Die off | 0 | 0 |
| Average slaughter weight (kg) | 109.5 | 112.3 |
| Feed uptake (kg) | 25 877 | 25 071 |
| Feed utilization (kg/kg) | 3.31 | 3.11 |

TABLE 11

Effect of the composition on the yield of store-pigs (The control group received individual antibiotic treatment by injection)

| | Control group | Experimental group |
|---|---|---|
| Number of animals | 100 | 100 |
| Initial average weight kg | 28.4 | 28.1 |
| Individuals treated by intramuscularly | 21 | 2 |
| Die off during the experiment | 0 | 0 |
| Slaughter weight kg | 105.8 | 109.8 |
| Feed utilization kg/kg | 3.23 | 2.96 |

In the first experiment, (Table 10), after the same length of fattening time, the slaughter weight in the experimental group was 2.8 kg higher, i.e. 2.6% on average, compared to the control group, and the feed amount necessary to produce 1 kg live weight was 0.2 kg less, which means 6% increase in feed utilization.

In the second experiment (Table 11) the slaughter weight was 3.9% higher in the experimental group, while the feed utilization was better by a value of 9.1% in the experimental group that that of the control group.

EXAMPLE 23—PILOT FEEDING EXPERIMENT WITH A COMPOSITION CONTAINING COPPER $(H_2O)_2$ BIS-GLYCINATE

Experimental feeding was performed with growing pigs, under pilot environmental conditions with the animal paired methods on a stock infected with the pathogen *Lawsonia intracellularis*. The control group received the usual antibiotic supplement mixed into the feed. The feed of the experimental group was supplemented with a composition of copper diammonium his-glycinate on a carrier, in a rationing of 1 kg/t.

The parameters studied: number of treatments, development of losses, average slaughter weight, and feed utilization.

TABLE 12

Effect of the treatment on the yield in paired-animal experiment.

| | Experimental group | Control |
|---|---|---|
| Number of animals | 326 | 331 |
| Days of fattening | 101 | 101 |
| Initial average weight kg | 30.86 | 33.74 |
| Added weight kg | 76.15 | 71.73 |

TABLE 12-continued

Effect of the treatment on the yield in paired-animal experiment.

| | Experimental group | Control |
|---|---|---|
| Average slaughter weight kg | 107.01 | 105.47 |
| Feed utilization kg/kg | 3.10 | 3.31 |

The slaughter weight in the experimental group was higher by 1.6%. The added weight in the experimental group was higher by 6.2%. The feed utilization in the experimental group was better by a value of 6.8% in the experimental group that that of the control group.

EXAMPLE 24—PILOT EXPERIMENTS WITH COPPER AMMONIA BIS-GLYCINATE CHELATE ON A FARM SHOWING THE SYMPTOMS OF NECROTIC *ENTERITIDIS* CAUSED BY *CLOSTRIDIUM PERFRINGENS* INFECTION

The experiments were carried out in two barns, holding 17 100 ROSS-308 baby chicks each. The farm is plagued continually with *Clostridium perfringens* infection. It requires antibiotic treatments in batches.

The first barn held the individuals of the control group, whereas the second barn held the individuals of the experimental group. The control group did not receive supplement in its feed. The flock held in the experimental barn had a feed supplemented with copper diammonium bis-glycinate applied onto a carrier in a dose of 1.0 kg/t.

The results are summarized in the Table 13.

TABLE 13

Effect of feeding the experimental composition on raising broilers

| Parameter studied | Control group | Experimental group | Difference |
|---|---|---|---|
| Days of raring | 42 | 42 | |
| Chicks at start | 17 100 | 17 100 | |
| Chicken shipped | 16 242 | 16 238 | 4 |
| Total living weight, kg | 31 005 | 32 395 | 1390 (4.5%) |
| Total weight gain, kg | 30 298 | 31 681 | 1383 (4.6%) |
| Total feed use, kg | 59 260 | 59 880 | 620 |
| Mean slaughter weight, g | 1909 | 1995*** | 86 (4.5%) |
| Relative feed utilization kg/kg | 1.96 | 1.89 | 3.6% |

***= the difference is significant at $P \leq 0.001$

The weight gain of the experimental group exceeded that of the control group by 4.6% while the experimental meat hybrid chicken required 3.6% less feed for the unit live weight gain.

The faces of the animals in the experimental group was well formed, no signs of a change indicating diarrhea was visible. The litter was somewhat drier in this group, the ammonia level of the air was perceptionally lower than that of the control.

No adverse side effects were observed when feeding the experimental composition.

EXAMPLE 25—EFFECT OF FEEDING COPPER AMMONIUM ETHYLENEDIAMINE TETRAACETIC ACID IN A FLOCK OF EGG LAYING HENS AFTER *CLOSTRIDIUM PERFRINGENS* CHALLENGE

Under laboratory conditions 108, 32 week old egg laying hens were placed into cages, with an animal density of 3 hens par cage. Before entering the birds into the experiment, cloacal swabs were used to test for the pathogen *Clostridium perfringens*. It was established that the flock is moderately infected by *Clostridium perfringens*.

Three equal groups were formed from the 108 birds with 36 egg laying hen in each.
1. Negative control group I *C. perfringens* negative
2. Positive control group II *C. perfringens* positive, inoculated by a gastric probe with 2 ml $10^6$ CFU/ml *C. perfringens* bacterial culture.
3. Supplemented, treatment group III *C. perfringens* positive, inoculated by a gastric probe with 2 ml $10^6$ CFU/ml *C. perfringens* bacterial culture.

The results are shown in Table 14.

TABLE 14

Yield parameters of egg laying hens challenged by *C. perfringens*.

| Data | Negative control group I | Positive control group II | Treatment group III |
|---|---|---|---|
| Total eggs (pc.) | 1750 | 1526 | 1868 |
| No. of eggs/hen | 48.60 | 42.38 | 51.80 |
| Total egg weight (kg) | 114.07 | 103.99 | 125.70 |
| Weight of egg g/pc. | 65.1 g | 68.1 g | 67.2 g |

The egg yield decreased by more than 13% in the positive control group, compared to the negative control group, due to the *C. perfringens* infection. In response to the treatment, the egg yield increased by 6.7% compared to the negative control group and by 22.4% compared to the positive control group. The total egg weight showed similar tendency during the experiment. There was a different trend in the measurement of individual eggs, because the individual egg weight was the largest in the positive control group.

EXAMPLE 26—FEEDING EXPERIMENT TO PREVENT DIARRHEAL DISEASES OCCURRING AT WEANING BY ADMINISTERING ZINC $(H_2O)_2$ MALEINATE 32 days old weaned piglets were fed by a feed supplemented with zinc ammonium maleinate. The experimental animals had *E. coli* infection. The control group received the standard antibiotic supplement in the feed to control the *E. coli* infection.

The production yields are shown in Table 15.

TABLE 15

Production yield parameters during the experiment

| | Control group | Experimental group |
|---|---|---|
| No. of animals | 28 | 31 |
| Initial weight (kg) | 9.11 | 9.19 |
| Duration of the experiment (days) | 45 | 38 |
| Die off during the experiment | 1 | 0 |
| Body weight at the end of the experiment (kg) | 21.26 | 24.05 |
| Daily weight gain (g) | 270 | 391 |
| Feed utilization (kg/kg) | 2.31 | 2.04 |

The average daily weight gain was 45% higher in the experimental group than in the control group. The feed utilization was 13% better in the experimental group than in the control group. There was no die off in the experimental group, however, in the control group 1 animal (3.6%) died during the experimental period.

REFERENCES

Chu, B. C, Garcia-Herrero, A., Johanson, T. H., Krewulak, K. D., Lau. C. K., Peacock, R. S., Slavinskaya, Z, Vogel, H. J.: Siderophore uptake in bacteria and the battle for iron with the host; a bird'eye view. Biometals(2010)23(4), 601-611.

Du, Z. (1994): Bioavailabilities of copper in copper proteinate, copper lysine and cupric sulfate, and copper tolerances of Holstein and Jersey cattle. Ph.D. Thesis, University of Kentucky, Lexington, Ky.

Kakukk Tibor, dr. Schmidt János, 1988. Takarmányozástan 3.4.:122-145

Leong, J. (1986) Siderophores: their biochemistry and possible role in the biocontrol of plant pathogens. Annu. Rev. Phytopathol., 24: 187-209.

Mahan et al. (1994): Biotechnology in the feed industry: Proc. of Alltech's Tenth Annual Symposium. p. 323-333

Miethke and Marahiel, (2007) SIDEROPHORE-BASED IRON ACQUISITION AND PATHOGEN CONTROL, Microbiol. Mol. Biol Rev. 71(3), 413-451

Neilands, J. B. (1981) Microbial iron compounds. Annu. Rev. Biochem., 50: 715-731.

Neilands, J. B., Konopka, K., Schwyn, B., Coy, M., Francis, R. T., Paw, H., Bagg, A. (1987) Comparative biochemistry of microbial iron assimilation. In: Iron Transport in Microbes, Plants and Animals. (Winkelmann, G., van der elm, D., Neilands, J. B. Eds.), (VCH Verlagsgesellschaft, Weinheim, Germany) pp. 3-33.

Quinn P. J., Carter M. E., Markey B. K., Carter G R., 1994. Clinical Veterinary Microbiology. Wolfe Publishing, London Shi et al. (1995): Influence of iron oxide, iron sulfate and iron proteinate on Cu bioavailabilities from Cu sulfate and Cu proteinate. J. Dairy Sci. 78: 187 (Suppl. 1).

Weger, L. A. de, Boxtel, R. van, Burg, B. van der, Gruters, R., Geels, E P., Schippers, B., Lugtenberg, B. (1986) Siderophores and outer membrane proteins of antagonistic, plant-growth-stimulating, root-colonizing *Pseudomonas* spp. J. Bacteriol., 165: 585-594.

Whittaker et al. (1993) Regul Toxicol Pharmacol., 18(3), 419-27

The invention claimed is:
1. A method for the inhibition of pathogenic bacteria proliferating in the small intestine part of the digestive tract and causing diseases therein or on the surface of the skin, and/or for the treatment of a disease caused by said bacteria, said method comprising administering to an animal selected from the group consisting of poultry, swine and bovine, an effective amount of the compound or a composition comprising the compound of general formula

$(M)_n(X)_m(Y)_o$ wherein M is selected from Zn, Cu, Fe, Mn or Ag;
X is $NH_3$ or $H_2O$;
Y is an amino acid, a fatty acid, a hydroxy acid and/or a polyamino-carboxylic acid;
n is 1-6;
m is 1-6;
o is 1-8
wherein the compound is obtained from compound $MCO_3$ or $M(NH_4)_2CO_3$, respectively, and wherein the compound is selected form the group consisting of: copper $(H_2O)$ bis-glycinate, copper $(H_2O)_2$ bis-glycinate, Cu$(H_2O)$ bis-malate, zinc $(H_2O)$ bis-glycinate, zinc $(H_2O)_2$ malate, Zn$(H_2O)$ bis-alaninate, Zn$(H_2O)$ bis-aspartate, Zn$(H_2O)$ bis-butyrate, Zn$(H_2O)$ bis-glutamate, Zn(H$_2$O) bis-propionate, Zn(H$_2$O) bis-valerianate, Zn(H$_2$O) bis-malate, copper (NH$_3$)$_2$ bis-glycinate, copper (NH$_3$)$_2$ bis-malate, Cu(NH$_3$)$_2$ asparaginate, Cu(NH$_3$)$_2$ bis-asparaginate, Cu(NH$_3$)$_2$ bis-glutamate, Cu(NH$_3$)$_2$ glutamate, zinc (NH$_3$)$_2$ bis-malate, zinc (NH$_3$)$_2$ malate, zinc (NH$_3$)$_2$ methionate, zinc (NH$_3$)$_4$ bis-glycinate, zinc (NH$_3$)$_4$ malate, Zn(NH$_3$)$_2$ asparaginate, Zn(NH$_3$)$_2$ aspartate, Zn(NH$_3$)$_2$ bis-asparaginate, Zn(NH$_3$)$_2$ bis-aspartate, Zn(NH$_3$)$_2$ bis-glutamate, Zn(NH$_3$)$_2$ bis-glycinate, Zn(NH$_3$)$_2$ bis-histidinate, Zn(NH$_3$)$_2$ citrate, and Zn(NH$_3$)$_2$ glutamate.

2. The method of claim 1 comprising administering to the animal a composition comprising the compound of the general formula, optionally together with standard additives.

3. The method of claim 1 wherein the compound of the general formula is administered to the animal, optionally together with standards additives, in releasable form from a suitable carrier material, powder and/or microgranulate, having a water content of no more than 12%.

4. The method according to claim 1, wherein the facultative pathogenic bacterium is selected from the group consisting of: *Salmonella, E. coli, Clostridium* sp., *Brachyspyra* sp., *Arcanobacterium* sp., *Staphylococcus* sp., *Streptococcus* sp., *Lawsonia* sp., *Eimerella* sp.

5. The method of claim 1 wherein Y is selected from the group consisting of
the 20 naturally occurring amino acids,
formic acid, acetic acid, propionic acid,
malic acid, lactic acid, and
nitrilotriacetic acid.

6. The method of claim 1, wherein X is complexed to M as an O-chelate or N-chelate ligand.

7. The method of claim 1 wherein the disease is selected from the group consisting of: poultry enteric diseases, swine enteric diseases, bovine enteric diseases, as well as superficial treatments, mastitis of dairy cattle, metritis of dairy cattle, hoof lesions of ungulates, enteric and superficial diseases of other animals.

8. The method according to claim 7, wherein the compound is selected from the group consisting of: zinc tetraammine bis-glycinate chelate, zinc malate chelate, zinc diammine malate chelate, zinc tetraammine malate chelate, zinc diammine methionate chelate, copper diammine lysinate chelate, and zinc diammine aminate chelate.

9. The method according to claim 7, wherein the compound is selected from the group consisting of zinc monoglycinate chelate, zinc bis-glycinate chelate, copper mono-glycinate chelate, copper bis-glycinate chelate, zinc diammine bis-malate chelate, zinc bis-malate chelate, and copper bis-malate chelate.

10. The method according to claim 7, wherein the compound is selected from the group consisting of zinc monoglycinate chelate, copper mono-glycinate chelate, and zinc diammine bis-malate chelate.

11. The method according to claim 7, wherein the compound is selected from the group consisting of copper diammine bis-malate, zinc (H$_2$O)$_2$ malate chelate, copper (H$_2$O)$_2$ bis-glycinate chelate copper (H$_2$O)$_2$ bis-glycinate chelate and copper amine bis-glycinate chelate.

12. A method for the treatment of a disease selected from the group consisting of: poultry enteric diseases, swine enteric diseases, bovine enteric diseases, as well as superficial treatments, mastitis of dairy cattle, metritis of dairy cattle, hoof lesions of ungulates, enteric and superficial diseases of other animals, for the inhibition of bacteria proliferating in the small intestine part of the digestive tract or on the surface of the skin and causing diseases therein, for the treatment of a disease caused by said bacteria, or for increasing body-weight gain and/or increasing feed utilization and/or increasing egg yield and/or decreasing mortality in the population of poultry and/or swine and/or dairy cow, said method comprising administering to an animal selected from the group consisting of poultry, swine and bovine an effective amount of the compound of general formula $$(M)_n(X)_m(Y)_o$$

wherein M is Zn, Cu, Fe, Mn or Ag;
X is NH$_3$ or H$_2$O;
Y is an amino acid, a fatty acid, hydroxy acid and/or a polyamino-carboxylic acid;
n is 1-6;
m is 1-6;
o is 1-8
wherein the complex is selected form the group consisting of:
copper (H$_2$O) bis-glycinate, copper (H$_2$O)$_2$ bis-glycinate, Cu(H$_2$O) bis-malate, zinc (H$_2$O) bis-glycinate, zinc (H$_2$O)$_2$ malate, Zn(H$_2$O) bis-alaninate, Zn(H$_2$O) bis-aspartate, Zn(H$_2$O) bis-butyrate, Zn(H$_2$O) bis-glutamate, Zn(H$_2$O) bis-propionate, Zn(H$_2$O) bis-valerianate, Zn(H$_2$O) bis-malate, copper (NH$_3$)$_2$ bis-glycinate, copper (NH$_3$)$_2$ bis-malate, Cu(NH$_3$)$_2$ asparaginate, Cu(NH$_3$)$_2$ bis-asparaginate, Cu(NH$_3$)$_2$ bis-glutamate, Cu(NH$_3$)$_2$ glutamate, zinc (NH$_3$)$_2$ bis-malate, zinc (NH$_3$)$_2$ malate, zinc (NH$_3$)$_2$ methionate, zinc (NH$_3$)$_4$ bis-glycinate, zinc (NH$_3$)$_4$ malate, Zn(NH$_3$)$_2$ asparaginate, Zn(NH$_3$)$_2$ aspartate, Zn(NH$_3$)$_2$ bis-asparaginate, Zn(NH$_3$)$_2$ bis-aspartate, Zn(NH$_3$)$_2$ bis-glutamate, Zn(NH$_3$)$_2$ bis-glycinate, Zn(NH$_3$)$_2$ bis-histidinate, Zn(NH$_3$)$_2$ citrate, and Zn(NH$_3$)$_2$ glutamate.

* * * * *